United States Patent
Kubota et al.

(10) Patent No.: US 10,806,417 B2
(45) Date of Patent: Oct. 20, 2020

(54) RADIOGRAPHIC IMAGING APPARATUS, RADIOGRAPHIC IMAGING SYSTEM AND INFORMATION PROCESSING METHOD

(71) Applicant: KONICA MINOLTA, INC., Chiyoda-ku, Tokyo (JP)

(72) Inventors: Tetsuo Kubota, Kokubunji (JP); Kazuhiko Katsushima, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 46 days.

(21) Appl. No.: 15/950,567

(22) Filed: Apr. 11, 2018

(65) Prior Publication Data

US 2018/0317872 A1 Nov. 8, 2018

(30) Foreign Application Priority Data

May 8, 2017 (JP) .................................. 2017-092168
Jul. 27, 2017 (JP) .................................. 2017-145009

(51) Int. Cl.
*H05G 1/64* (2006.01)
*A61B 6/00* (2006.01)

(52) U.S. Cl.
CPC .............. *A61B 6/46* (2013.01); *A61B 6/4233* (2013.01); *A61B 6/461* (2013.01); *A61B 6/563* (2013.01); *A61B 6/4405* (2013.01); *A61B 6/4411* (2013.01)

(58) Field of Classification Search
CPC ... A61B 6/4233; A61B 6/4405; A61B 6/4411; A61B 6/46; A61B 6/461; A61B 6/563;
(Continued)

(56) References Cited

U.S. PATENT DOCUMENTS 8,107,590 B2   1/2012  Nishino et al.
9,195,507 B1 * 11/2015  Doyle ................... G06F 9/5027
(Continued)

FOREIGN PATENT DOCUMENTS

JP   2010051523 A   3/2010
JP   2016101210 A   6/2016
WO  2014098398 A1   6/2014

OTHER PUBLICATIONS

Extended European Search Report (EESR) dated Jul. 31, 2018 issued in counterpart European Application No. 18167263.5.
(Continued)

*Primary Examiner* — Irakli Kiknadze
(74) *Attorney, Agent, or Firm* — Holtz, Holtz & Volek PC

(57) ABSTRACT

A radiographic imaging apparatus includes a radiation detector, a reader and a hardware processor. The radiation detector includes a substrate. On the substrate, radiation detection elements are arranged two-dimensionally. The radiation detection elements generate amounts of electric charges corresponding to doses of radiation by being irradiated with the doses of the radiation. The reader reads the amounts of the electric charges generated by the respective radiation detection elements as signal values, and generates image data based on the signal values. The hardware processor communicates with a portable terminal having a web browser, generates web content displayable on the web browser in response to a request from the portable terminal, and sends at least one of the web content and the image data to the portable terminal in response to the request from the portable terminal.

6 Claims, 16 Drawing Sheets

(58) Field of Classification Search
CPC ......... A61B 6/145; H04L 67/02; H04L 67/42; H04N 2005/2255; H04N 5/23206; H04N 5/32; H04N 5/2254; H04N 5/2256; H04N 5/23245; H04N 5/2351; H04N 5/2354; H04N 5/33; H04N 5/332; H04N 9/045; H04N 9/735; H04N 5/30; H04N 5/23219; H04N 19/86; H04N 1/6077; H04N 1/6086; H04N 5/23212; H04N 5/23293; H04N 7/144; H04N 1/0014; H04N 1/00151; H04N 1/00164; H04N 1/00167; H04N 1/00244; H04N 2201/0094; H04N 1/00307; H04N 2201/0096; H04N 1/32128; H04N 1/387; H04N 2201/0055; H04N 1/00347; H04N 2201/3252; H04N 1/00204; H04N 1/3878; H04N 2201/0084; H04N 5/232; G01T 1/16; G06F 19/321; G06F 3/04845; G06F 3/04847; G06T 11/001; G06T 2210/41; G06T 2207/20064; G06T 5/002; G06T 5/10; G09G 2320/0271; G09G 2320/0693; G09G 2354/00; G09G 2380/08; G09G 5/026; G09G 5/06; G09G 5/14; H04B 3/54; G02B 5/208; H04W 48/16; H04W 4/21; H04W 4/80; H04W 76/14; A61K 31/4164; A61K 31/4174; A61K 47/10; A61K 47/12; A61K 47/14; A61K 47/183; A61K 47/44; A61K 9/0014; A61K 9/06; A61K 9/107; A61P 17/00

USPC ................................. 378/98.2, 62, 4, 19, 98
See application file for complete search history.

(56) References Cited

U.S. PATENT DOCUMENTS

| | | | |
|---|---|---|---|
| 2004/0002302 A1* | 1/2004 | Takemoto | H04N 1/0014 455/3.06 |
| 2008/0239139 A1* | 10/2008 | Choi | H04N 5/23293 348/345 |
| 2012/0147045 A1* | 6/2012 | Oike | G06F 3/0483 345/634 |
| 2013/0018666 A1* | 1/2013 | Murphy | G16H 20/40 705/2 |
| 2014/0369664 A1* | 12/2014 | Azami | G11B 27/32 386/239 |
| 2015/0237106 A1 | 8/2015 | Golay | |
| 2016/0253455 A1 | 9/2016 | Hasegawa et al. | |
| 2018/0198930 A1* | 7/2018 | Tokiwa | H04N 1/00222 |

OTHER PUBLICATIONS

European Office Action dated Feb. 22, 2019 issued in counterpart European Application No. 18167263.5.
European Office Action dated Jul. 17, 2019 issued in European Application No. 18 167 263.5.
European Office Action dated May 12, 2020 issued in European Application No. 18167263.5.

* cited by examiner

FIG.3

| CONTENTS OF REQUEST | COOPERATIVE DESTINATION | COOPERATIVE DESTINATION URL | DATA TYPE | DATA MANIPULATION |
|---|---|---|---|---|
| DISPLAY PATIENT LIST (PORTABLE TERMINAL) | EXTERNAL SYSTEM | http://xxx.xxx.xxx.xxx/Patient | PATIENT INFORMATION | GET (OBTAIN) |
| DISPLAY MEDICAL CARE INFORMATION (PORTABLE TERMINAL) | EXTERNAL SYSTEM | http://xxx.xxx.xxx.xxx/MedicalRecord | MEDICAL CARE INFORMATION | GET (OBTAIN) |
| FIX IMAGE (PORTABLE TERMINAL) | EXTERNAL SYSTEM | http://xxx.xxx.xxx.xxx/Image | TAKEN IMAGE | POST (SAVE) |
| ... | ... | ... | ... | ... |

FIG.5A

| PATIENT ID | NAME | REQUESTED DEPARTMENT | |
|---|---|---|---|
| WARD | IMAGING SITE | COMMENTS ON IMAGING | ←34 |

| REQUESTED DEPARTMENT | NOT NARROWED > |
|---|---|
| WARD | NOT NARROWED > |

L {
| 0001 | TARO NIHON | INTERNAL MEDICINE DEPARTMENT |
|---|---|---|
| | CHEST STANDING POSITION·P→A | COMMENTS ON EXAMINATION |
| 0002 | ICHIRO AOKI | ORTHOPAEDICS DEPARTMENT |
| | CHEST STANDING POSITION·P→A | COMMENTS ON EXAMINATION, PATIENT 00 |
| 0003 | JIRO ITO | RESPIRATORY MEDICINE DEPARTMENT |
| | CHEST STANDING POSITION·P→A | COMMENTS ON EXAMINATION, PATIENT 00 |
| 0004 | SABURO UEDA | INTERNAL MEDICINE DEPARTMENT |
| | CHEST STANDING POSITION·P→A | COMMENTS ON EXAMINATION, PATIENT 00 |

[ ] [LOG OFF]    [UPDATE] [START EXAMINATION]

FIG.5B

| ID | 0001 | NAME | TARO NIHON | ←34 |
|---|---|---|---|---|
| REQUESTED DEPARTMENT | INTERNAL MEDICINE DEPARTMENT | WARD | | |
| RECEIPT NUMBER | 0000001 | COMMENTS | COMMENTS ON EXAMINATION | ←$I_1$ } $I$ |

$I_2$

✓ IMAGING IS AVAILABLE

CHEST STANDING POSITION·P→A    1/1

[PICTURE] [ ] [DISPLAY] [SUSPEND EXAMINATION] [END EXAMINATION]

RADIOGRAPHIC IMAGING APPARATUS, RADIOGRAPHIC IMAGING SYSTEM AND INFORMATION PROCESSING METHOD

BACKGROUND

1. Technological Field

This invention relates to a radiographic imaging apparatus, a radiographic imaging system including the radiographic imaging apparatus, and an information processing method using the radiographic imaging apparatus.

2. Description of the Related Art

Portable radiographic imaging systems have been developed. In general, a portable radiographic imaging system is constituted of, for example, a panel-shaped radiographic imaging apparatus (called an FPD (Flat Panel Detector)), a visiting cart carrying a radiation emission apparatus, and a portable console constituted of a laptop PC or the like. A user(s) (a radiologist, etc.) can take the system to an imaging location and perform a series of medical practice-related actions including imaging and image checking at the location. This makes it easy to perform radiographic imaging of a patient who is difficult to move.

However, this kind of portable radiographic imaging system is expensive. This is an obstacle to adopting the system for small-sized hospitals or clinics where imaging is not performed so often. Hence, attempts to reduce manufacturing cost of the system have been made by using a portable terminal instead of a dedicated portable console. (Refer to Japanese Patent Application Publications No. 2010-051523 (Patent Document 1) and No. 2016-101210 (Patent Document 2).)

In the system disclosed in Patent Document 1 or Patent Document 2, a radiographic imaging apparatus communicates with a console or the like via an in-hospital network. The system does not work under an environment where no communion network is provided.

Further, in the system disclosed in Patent Document 1 or Patent Document 2, input and viewing of diagnosis information and facility booking, input of radiographic imaging booking and so forth are performed on the screen of a portable terminal, whereas taken images for diagnosis are displayed on another apparatus (a display of the radiographic imaging apparatus in the case of the system disclosed in Patent Document 1, or a terminal of an external system 4 in the case of the system disclosed in Patent Document 2). Thus, depending on what to do, apparatuses to use need to be switched. This decreases efficiency of imaging and so forth.

By installing an application for imaging in a terminal apparatus, various kinds of information and taken images may be checked with a single apparatus (i.e. the terminal apparatus). However, depending on what to do, applications need to be switched. This can hardly increase efficiency of imaging and so forth.

SUMMARY

The present invention has been conceived in view of the above problems, and objects of the present invention include efficiently performing a series of medical practice-related actions including imaging and image checking in a radiographic imaging system that uses a portable terminal instead of a portable console.

In order to achieve at least one of the objects, according to an aspect of the present invention, there is provided a radiographic imaging apparatus including: a radiation detector including a substrate where radiation detection elements are arranged two-dimensionally, the radiation detection elements generating amounts of electric charges corresponding to doses of radiation by being irradiated with the doses of the radiation; a reader that reads the amounts of the electric charges generated by the respective radiation detection elements as signal values, and generates image data based on the signal values; and a hardware processor that: communicates with a portable terminal having a web browser; generates web content displayable on the web browser in response to a request from the portable terminal; and sends at least one of the web content and the image data to the portable terminal in response to the request from the portable terminal.

BRIEF DESCRIPTION OF THE DRAWINGS

The advantages and features provided by one or more embodiments of the present invention will become more fully understood from the detailed description given hereinbelow and the appended drawings which are given by way of illustration only, and thus are not intended as a definition of the limits of the present invention, wherein:

FIG. 3 shows a cooperation with external system 4 set table stored in a storage of the radiographic imaging apparatus shown in FIG. 2;

FIG. 5A shows an example of web content which the portable terminal shown in FIG. 4 displays;

FIG. 5B shows an example of the web content which the portable terminal shown in FIG. 4 displays;

DETAILED DESCRIPTION OF EMBODIMENTS

Hereinafter, one or more embodiments of the present invention will be described in detail with reference to the drawings.

A variety of limitations that are technically preferable for carrying out the present invention are put on the embodiments described below. However, the technical scope of the present invention is not limited to the disclosed embodiments or illustrated examples.

First Embodiment

First, a first embodiment of a radiographic imaging system of the present invention is described with reference to FIG. 1 to FIG. 7.

[Configuration of Radiographic Imaging System]

Figure 1:
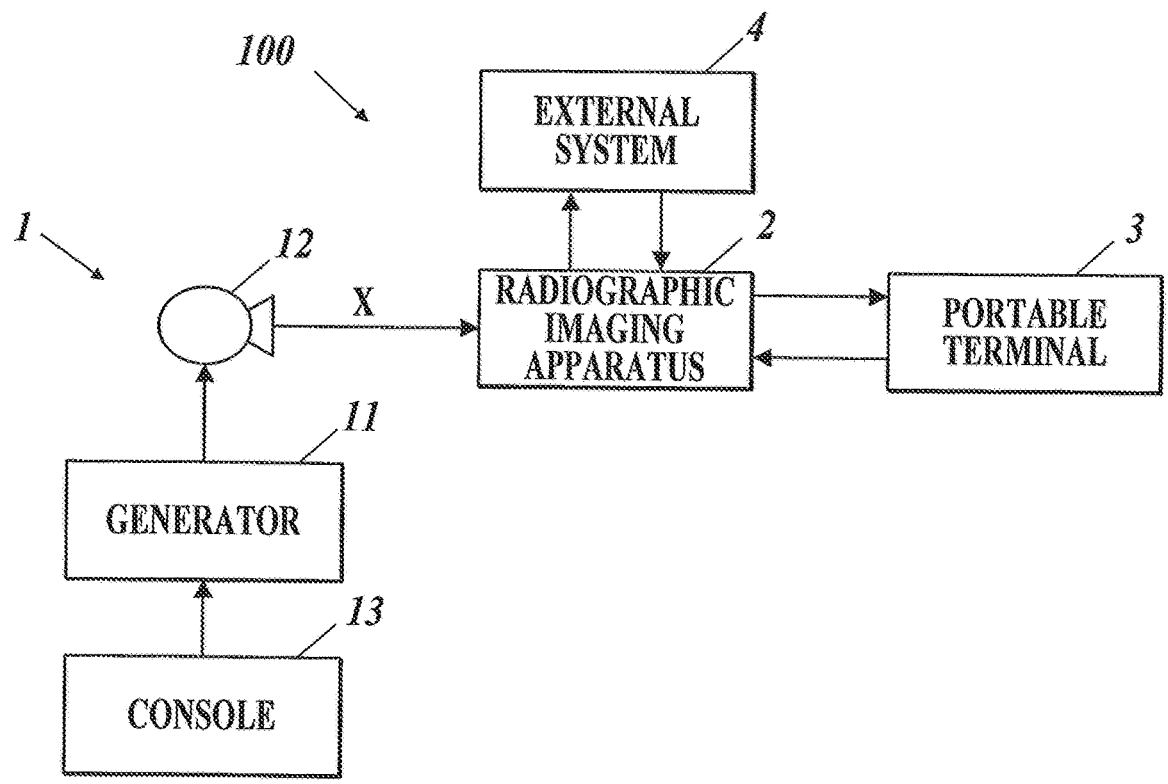
FIG. 1 is a schematic block diagram of a radiographic imaging system according to a first embodiment of the present invention.

First, configuration of a radiographic imaging system 100 of this embodiment is described. FIG. 1 is a schematic block diagram of the radiographic imaging system 100 of this embodiment.

As shown in FIG. 1, the radiographic imaging system 100 of this embodiment includes a radiation emission apparatus 1, a radiographic imaging apparatus 2 and a portable terminal 3.

The radiographic imaging system 100 does not require a console that controls the radiographic imaging apparatus 2, and can directly communicate with an external system 4. The external system 4 herein is a generic term used to refer to an electronic medical record system, a radiology information system (RIS), a picture archiving and communication system (PACS), an image processing system and so forth.

The radiation emission apparatus 1 includes a generator 11, a radiation source 12 and a console 13.

The generator 11 applies voltage corresponding to set tube voltage, tube current, emitting time (mAs value) and/or the like to the radiation source 12.

The radiation source 12 includes a not-shown rotating anode that generates radiation and a not-shown filament that emits electron beams to the rotating anode, and generates radiation X of an amount corresponding to the voltage applied by the generator 11.

The console 13 includes an operation unit and an exposure switch operable by a user (a radiologist, etc.). The console 13 sets various imaging conditions (conditions for radiation emission, such as tube voltage, tube current, emitting time and current-time product) on the basis of operations to the operation unit. Further, the console 13 instructs the generator 11 to start radiation emission (voltage application) or the like on the basis of an operation to the exposure switch.

The radiation emission apparatus 1 may be movable by being integrated with a visiting cart.

The radiographic imaging apparatus 2 reads image data when irradiated with the radiation emitted from the radiation emission apparatus 1, and stores the read image data in itself or sends the read image data to the portable terminal 3 or the external system 4.

The radiographic imaging apparatus 2 may be a dedicated type that is integrated with an imaging table, or may be a portable type (a cassette type), but preferably the portable type if the radiation emission apparatus 1 is movable.

The radiographic imaging apparatus 2 is detailed below.

The portable terminal 3 is for checking radiographs (taken images) taken by the radiographic imaging apparatus 2. The portable terminal 3 is not particularly limited in configuration, but preferably a commercially-available portable terminal, such as a smartphone or a tablet terminal.

The portable terminal 3 is communicably connected with one or more radiographic imaging apparatuses 2 and/or one or more external systems 4, and displays images for display (hereinafter called display-use images) based on the image data received from the radiographic imaging apparatus(es) 2 and/or the external system(s) 4.

The portable terminal 3 is detailed below.

[Configuration of Radiographic Imaging Apparatus]

Figure 2:
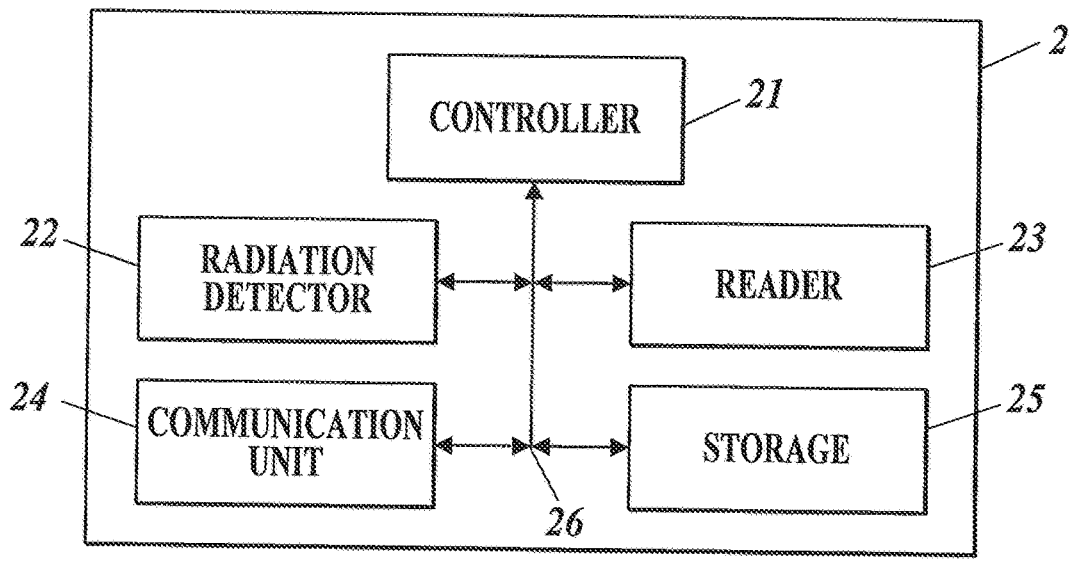
FIG. 2 is a block diagram showing a radiographic imaging apparatus of the radiographic imaging system shown in FIG. 1.

Next, the radiographic imaging apparatus 2 of the radiographic imaging system 100 is detailed. FIG. 2 is a block diagram of the radiographic imaging apparatus 2.

As shown in FIG. 2, the radiographic imaging apparatus 2 includes a controller 21, a radiation detector 22, a reader 23, a communication unit 24 and a storage 25, and these components 21 to 25 are connected to one another through a bus 26. A not-shown built-in power source supplies power to the components 21 to 25.

The controller 21 includes a CPU (hardware processor) and a RAM, and controls the overall operation of the components of the radiographic imaging apparatus 2. More specifically, on the basis of turning on of a power switch, reception of a predetermined control signal from the radiation emission apparatus 1, irradiation with radiation emitted from the radiation emission apparatus 1 or the like, the controller 21 (CPU) reads a process program(s) among various process programs stored in the storage 25, opens the read process program in the RAM, and performs a process among various processes in accordance with the opened process program.

The radiation detector 22 is not particularly limited and accordingly a well-known detector can be used as far as it has a substrate where radiation detection elements are arranged two-dimensionally. The radiation detection elements generate amounts of electric charges corresponding to doses of radiation by being irradiated with the radiation.

That is, the radiographic imaging apparatus 2 may be, what is called, an indirect type that includes a scintillator and detects light generated by the scintillator receiving radiation, or may be, what is called, a direct type that detects radiation directly without a scintillator.

Further, the radiographic imaging apparatus 2 may be a cooperative type that starts accumulation of electric charges on the basis of a signal from the radiation emission apparatus 1, or may be a non-cooperative type that starts accumulation of electric charges by detecting radiation by itself without a signal from the radiation emission apparatus 1.

The reader 23 is not particularly limited and accordingly a well-known reader can be used as far as it can read the amounts of electric charges generated by the respective radiation detection elements as signal values and generate image data on the basis of the signal values.

The communication unit 24 includes a network interface, and sends/receives data to/from the portable terminal 3 connected therewith via a communication network, such as a LAN (Local Area Network) or the Internet.

The communication unit 24 may include a communication interface for close range wireless communication or the like, such as Bluetooth® or NFC, so as to send/receive data to/from the portable terminal 3 using the close range wireless communication or the like under an environment where the above communication network is not provided or disconnected. Alternatively, the communication unit 24 (radiographic imaging apparatus 2) may be connected with the portable terminal 3 by a wired system.

Further, a not-shown public line communication unit may be provided to perform communication via a public line(s) so that the radiographic imaging apparatus 2 can directly communicate with the external system 4 other than the portable terminal 3.

The storage 25 includes an HDD (Hard Disk Drive), a semiconductor memory and/or the like, and stores therein various process programs (various image processing programs, a web server program, etc.), parameters and files necessary for execution of the programs, and so forth.

The storage 25 also stores therein the image data generated by the reader 23 as well as imaging order information (patient information on each patient to be imaged, an imaging site(s), an imaging direction(s), various imaging conditions, etc.) linked with the image data.

The image data may also be linked with, for example, comments on imaging.

The storage 25 also stores therein a cooperation with external system 4 set table. This cooperation with external system 4 set table is, as shown in FIG. 3 as an example, a table where contents of each request from the portable terminal 3 is correlated with: among various systems of the external system 4, a cooperative server with which the radiographic imaging apparatus 2 cooperates for the request; a URL of the cooperative server; a type of information to send/receive to/from the radiographic imaging apparatus 2; and a type of manipulation on the information.

The controller 21 of thus-configured radiographic imaging apparatus 2 performs the following operation in accordance with the process program(s) stored in the storage 25.

For example, the controller 21, through the communication unit 24, receives a list of patients (hereinafter called a patient list) and medical care information (both external information) from the external system 4, and receives contents of adjustment to be performed on the image data from the portable terminal 3.

The medical care information contains the overall information on each patient managed by, what is called, an electronic medical record. That is, the medical care information contains, in addition to basic information on each patient, information on a symptom(s), an examination(s), diagnosis, a treatment plan(s), another or other medical facilities that the patient has visited, a doctor(s) in charge, and so forth.

Further, the controller 21 sends the generated image data and medical care information to the portable terminal 3 through the communication unit 24. The image data may be output automatically as soon as the image data is/are generated, or may be output in response to a sending request from the outside. Further, the image data may be divided and output in multiple times.

The above operation makes the controller 21 function as a first communication unit of the present invention together with the communication unit 24.

Further, the controller 21 can send the image data and various signals (e.g. signals to request the patient list and the medical care information) to the external system 4 via the portable terminal 3 by using a tethering function of the portable terminal 3.

Further, the controller 21 can receive the patient list and the medical care information from the external system 4 via the portable terminal 3 by using the tethering function of the portable terminal 3.

That is, the controller 21 also functions as a second communication unit of the present invention together with the communication unit 24 and the portable terminal 3.

The radiographic imaging apparatus 2 of this embodiment communicates with the portable terminal 3 by using the first communication unit, and communicates with the external system 4 by using the second communication unit, and information sent/received to/from the portable terminal 3 from/to the external system 4 passes through the radiographic imaging apparatus 2. That is, the radiographic imaging apparatus 2 serves as a gateway in the radiographic imaging system 100 of this embodiment.

If the radiographic imaging apparatus 2 includes the public line communication unit as described above, the public line communication unit and the communication unit 24 may be used for different purposes, namely, for communication with the external system 4 and for communication with the portable terminal 3, respectively. In this case, the controller 21 functions as the second commination unit of the present invention together with the public line communication unit.

Further, the controller 21 may have a function of obtaining one or more past image data from the external system 4 (PACS, etc.) through the communication unit 24. Each past image data contains the imaging conditions (kV, mAs, SID, presence or absence of a grid(s), presence or absence of an added filter(s), a type of the added filter(s), distance between the radiation source and the detector, necessity or unnecessity of a grid(s), presence or absence of automatic exposure control, etc.) and an image processing parameter(s).

Further, the controller 21 may have a function of restarting to upload data at the time of restart of communication with the external system 4 if the communication with the external system 4 is once disconnected.

Further, the controller 21 performs, automatically or in response to a request from the portable terminal 3, predetermined image processing on Raw image data generated by the reader 23, thereby generating at least one type of processed image data. That is, the controller 21 functions as an image generation unit of the present invention.

The image processing performed here is divided into two types mainly that are a correction process and a display-use image generation process. Examples of the correction process include offset correction, gain correction, defect correction and scattered ray removal. Examples of the display-use image generation process include noise reduction, frequency processing, gradation processing, spatial transformation (rotation/inversion) and resolution conversion (a process to generate thinned-out images for preview). These can generate various display-use images (image data for preview generated by a simple process and image data for diagnosis generated by a full process).

Instead of the radiographic imaging apparatus 2, the portable terminal 3 or the external system 4 may have the image processing function.

Alternatively, two or more of the radiographic imaging apparatus 2, the portable terminal 3 and the external system 4 may have the image processing function, and an apparatus to perform the image processing may be determined on the basis of their processing performances, communication speeds and/or the like.

Still alternatively, two or more of the radiographic imaging apparatus 2, the portable terminal 3 and the external system 4 may have the image processing function, and the apparatuses having the image processing function may perform, in parallel, multiple types of the image processing that can be performed in arbitrary order.

Further, the controller 21 generates web content containing the display-use image(s) in response to a request from the portable terminal 3. That is, the controller 21 functions as a content generation unit of the present invention.

The web content generated by the controller 21 contains data obtained from the external system 4 and processed. Data of the web content may contain a process program(s) executable on web browsers. If the process program is sent as the web content, it is preferable that the process program be in the form of JavaScript® or WebAssembly executable on web browsers.

The controller 21 sends the generated web content to the portable terminal 3 through the communication unit 24.

When the processed image data is stored, the controller 21 may store the processed image data together with the parameter used in the image processing for generating the processed image data. This enables immediate image processing on image data if the need to re-perform the same image processing on the same Raw image data arises in the feature.

Among the processed image data, those generated at low processing cost may not be stored in the storage 25, and only the parameter used in the image processing may be stored therein. This is because the image processing the processing cost of which is low does not take much time or effort even if the image processing is performed every time it is required, as compared with the image processing the processing cost of which is high. Consequently, capacity of the storage 25 of the radiographic imaging apparatus 2 can be saved.

[Configuration of Portable Terminal]

Figure 4:
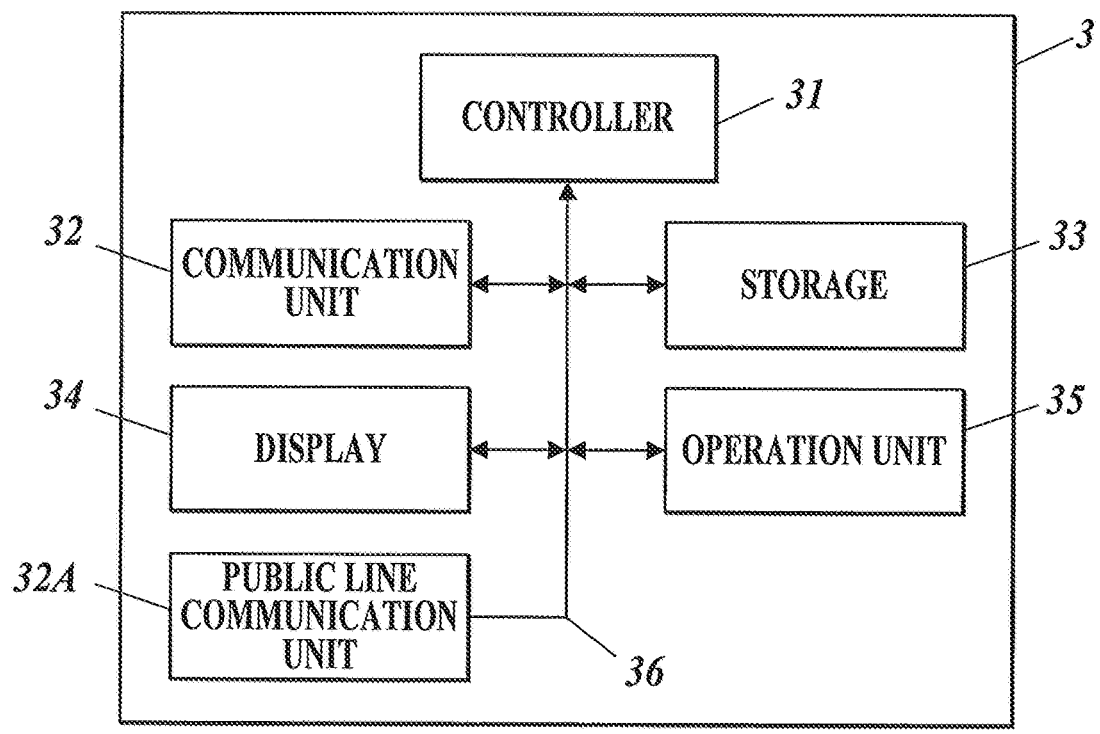
FIG. 4 is a block diagram showing a portable terminal of the radiographic imaging system shown in FIG. 1.

Next, the portable terminal 3 of the radiographic imaging system 100 is detailed. FIG. 4 is a block diagram showing configuration of the portable terminal 3.

As shown in FIG. 4, the portable terminal 3 includes a controller 31, a communication unit 32, a public line communication unit 32A, a storage 33, a display 34 and an operation unit 35, and these components 31 to 35 are connected to one another through a bus 36. A not-shown built-in power source supplies power to the components 31 to 35.

The controller 31 includes a CPU and a RAM, and controls the overall operation of the components of the portable terminal 3. More specifically, on the basis of input of an operation signal from the operation unit 35 or reception of any of various signals and/or data from the radiographic imaging apparatus 2, the controller 31 (CPU) reads a process program(s) among various process programs stored in the storage 33, opens the read process program in the RAM, and performs a process among various processes in accordance with the opened process program, or controls displayed contents on the display 34.

The communication unit 32 includes a network interface, and sends/receives data to/from apparatuses external to the portable terminal (the radiographic imaging apparatus 2 and the external system 4) connected therewith via a communication network, such as a LAN (Local Area Network) or the Internet.

The communication unit 32 may include a communication interface for close range wireless communication or the like, such as Bluetooth® or NFC, so as to send/receive data to/from the external apparatuses using the close range wireless communication or the like under an environment where the above communication network is not provided or disconnected. Alternatively, the communication unit 32 (portable terminal 3) may be connected with the external apparatuses by a wired system.

The public line communication unit 32A includes an antenna, and sends/receives data to/from the external system 4 using radio waves for a public line(s).

If the radiographic imaging apparatus 2 includes the second communication unit as described above, as the portable terminal 3, one not having this public line communication unit 32A (e.g. one dedicated for Wi-fi) may be used. Further, if an in-hospital network can be used, the portable terminal 3 may communicate with the external system 4 using the in-hospital network instead of the public line.

The storage 33 includes an HDD (Hard Disk Drive), a semiconductor memory and/or the like, and stores therein various process programs (system programs and application programs, such as a web browser(s)), parameters and files necessary for execution of the programs, and so forth.

The display 34 includes a monitor, such as an LCD, and displays various screens in accordance with instructions of display signals input from the controller 31.

The operation unit 35 includes a pointing device, such as a keyboard including various keys or a mouse, or a touchscreen placed on the display 34, and outputs, to the controller 31, input operation signals corresponding to key operations to the keyboard or mouse operations, or corresponding to positions of touch operations to the touchscreen.

The controller 31 of thus-configured portable terminal 3 performs the following operation in accordance with the process program(s) stored in the storage 33.

For example, the controller 31 receives data of various kinds of web content from the radiographic imaging apparatus 2 through the communication unit 32.

Further, the controller 31 accepts, on the web browser, operations (input operations, selection operations, etc.) to the operation unit 35, and sends their contents (the input or selected imaging order information, instructions to adjust the input or selected image data, etc.) to the radiographic imaging apparatus 2.

Further, the controller 31 relays communication between the radiographic imaging apparatus 2 and the external system 4 through the communication unit 32 and the public line communication unit 32A. That is, the controller 31 has the tethering function.

The controller 31 displays, on the display 34, an imaging order information list screen L shown in FIG. 5A, a medical care information screen I shown in FIG. 5B and so forth on the basis of the received data of the web content.

Figure 6A:
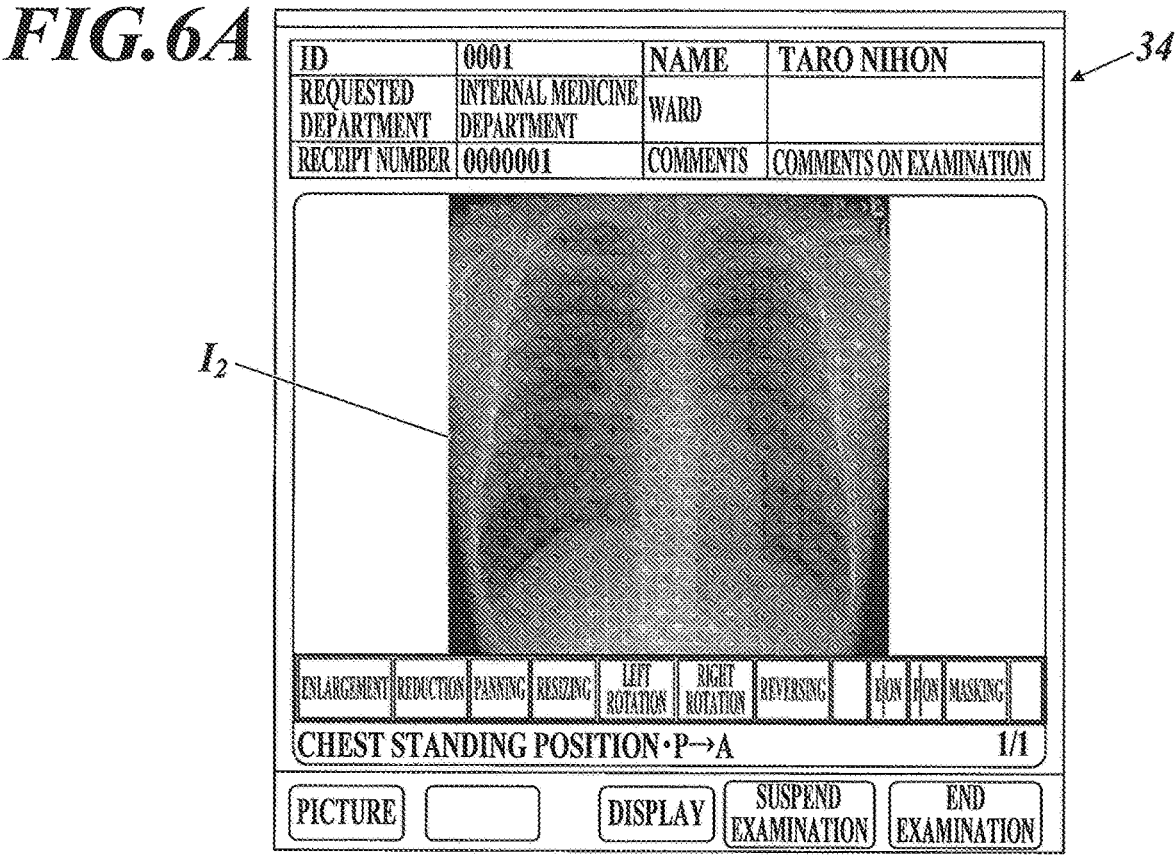
FIG. 6A shows an example of the web content which the portable terminal shown in FIG. 4 displays.
Figure 6B:
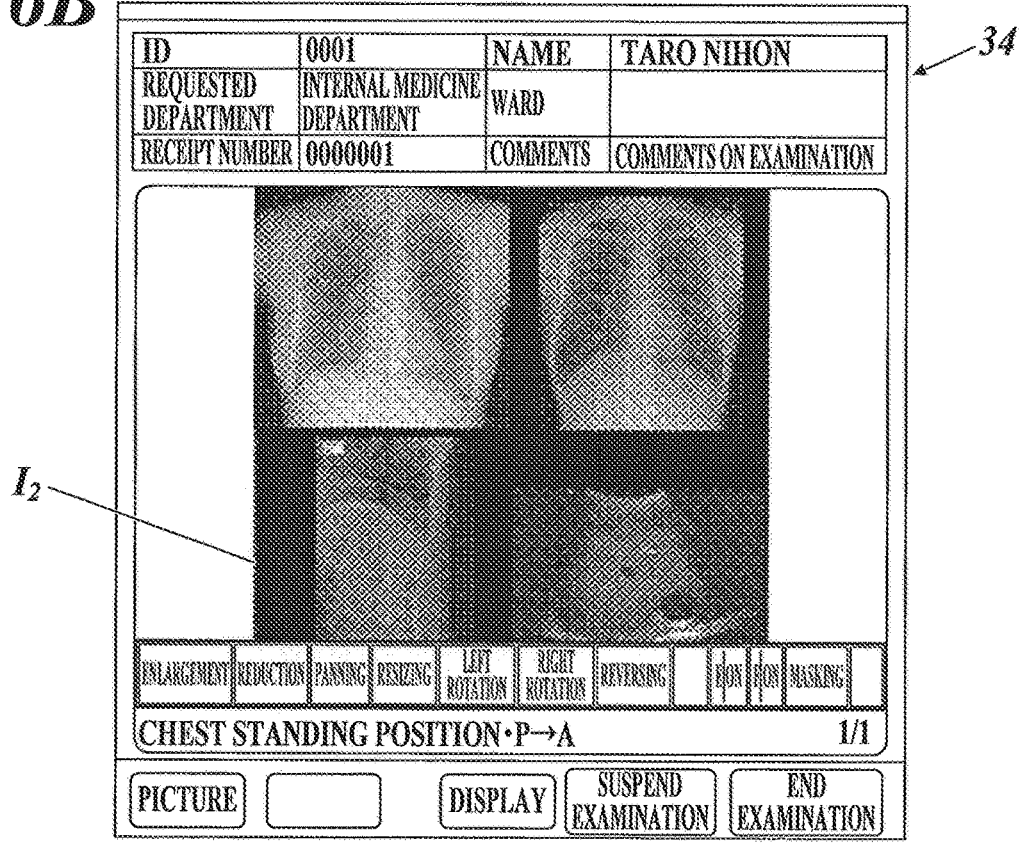
FIG. 6B shows an example of the web content which the portable terminal shown in FIG. 4 displays.

In the medical care information screen I of this embodiment, a base region $I_1$ and a changeable region I2 are provided. In the base region $I_1$, the patient information on a patient, the imaging conditions and/or the like are displayed, whereas in the changeable region I2, as shown in FIG. 6A, a taken image, a medical record of the patient and/or the like are displayed. Alternatively, in the changeable region $I_2$, as shown in FIG. 6B, multiple types of images (e.g. images of diffident sites of the same patient) may be displayed at a time.

The web content, which is displayed on the display 34, is generated by the radiographic imaging apparatus 2 mainly, but the web content generated by the external system 4 may be displayed thereon. If the medical care information screen I described in this embodiment is displayed thereon, the base region $I_1$ may be generated by the radiographic imaging apparatus 2, and the web content generated by the external system 4 or the web content generated such that the radiographic imaging apparatus 2 processes data received from the external system 4 may be fitted in the changeable region $I_2$.

The list screen L, the medical care information screen I and so forth may be displayed by a console application separately installed in the portable terminal 3. In this case, the portable terminal 3 has a function of receiving image data from the radiographic imaging apparatus 2 and storing the image data in the storage 33.

Conventionally, every time the displayed contents are switched, applications or tabs of a browser need to be switched. However, like this embodiment, by making the radiographic imaging apparatus 2 serving as the gateway, the displayed contents can be switched on the same tab or application, and accordingly a seamless operation becomes available.

If the radiographic imaging apparatus 2 has a function of also storing the parameter used in the image processing, visibility of overlay display or the like may be changed between a case where the parameter of the past image(s) is automatically carried on and a case where the parameter is adjusted manually.

When an image(s) is adjusted, the current value of the parameter for adjustment may be displayed.

If the radiographic imaging apparatus 2 has a function of obtaining the past image data from the external system 4, the past image(s) based on the past image data may be displayed on the display 34. In this case, a list of the past images may be displayed on the display 34 and the list and the past image(s) may be switchable and/or the past images may be switchable, or as shown in FIG. 6B, the past image(s) may be displayed together with a currently taken image(s).

Together with the past image(s), the past imaging conditions and/or the past image processing parameter(s) may be displayed (overlaid or the like). Consequently, what kind of imaging has been performed in the past can be refereed to.

If the web content contains the process program(s) executable on the web browser, the web content may contain, as the process program, a process of performing image correction (gain correction, offset correction, defect correction or the like) on the image data received from the radiographic imaging apparatus 2. This can correct individual difference in image data caused by being generated by different radiographic imaging apparatuses 2.

The process program may contain a process of caching the once-obtained process program in the web browser or re-obtaining the process program only if its version is different from the current one. This eliminates the need to receive the same process program to perform the same image processing, and hence is preferable in terms of speeding up of display.

Further, the process program may contain a process of omitting a part of the image processing to be performed or returning a part of the image processing to be performed to the radiographic imaging apparatus 2 such that the radiographic imaging apparatus 2 performs the part, depending on the degree of importance of the image processing or the processing cost. This prevents excessive workload of the controller 31 of the portable terminal 3.

Further, the process program may contain a process of deleting the image data and the parameter stored in the storage 33 on the basis of an operation to end the web browser or to end imaging. This leaves, after imaging, no personal information on the patient in the portable terminal 3, and hence is preferable in terms of security.

[Operation of Radiographic Imaging System]

Figure 7:
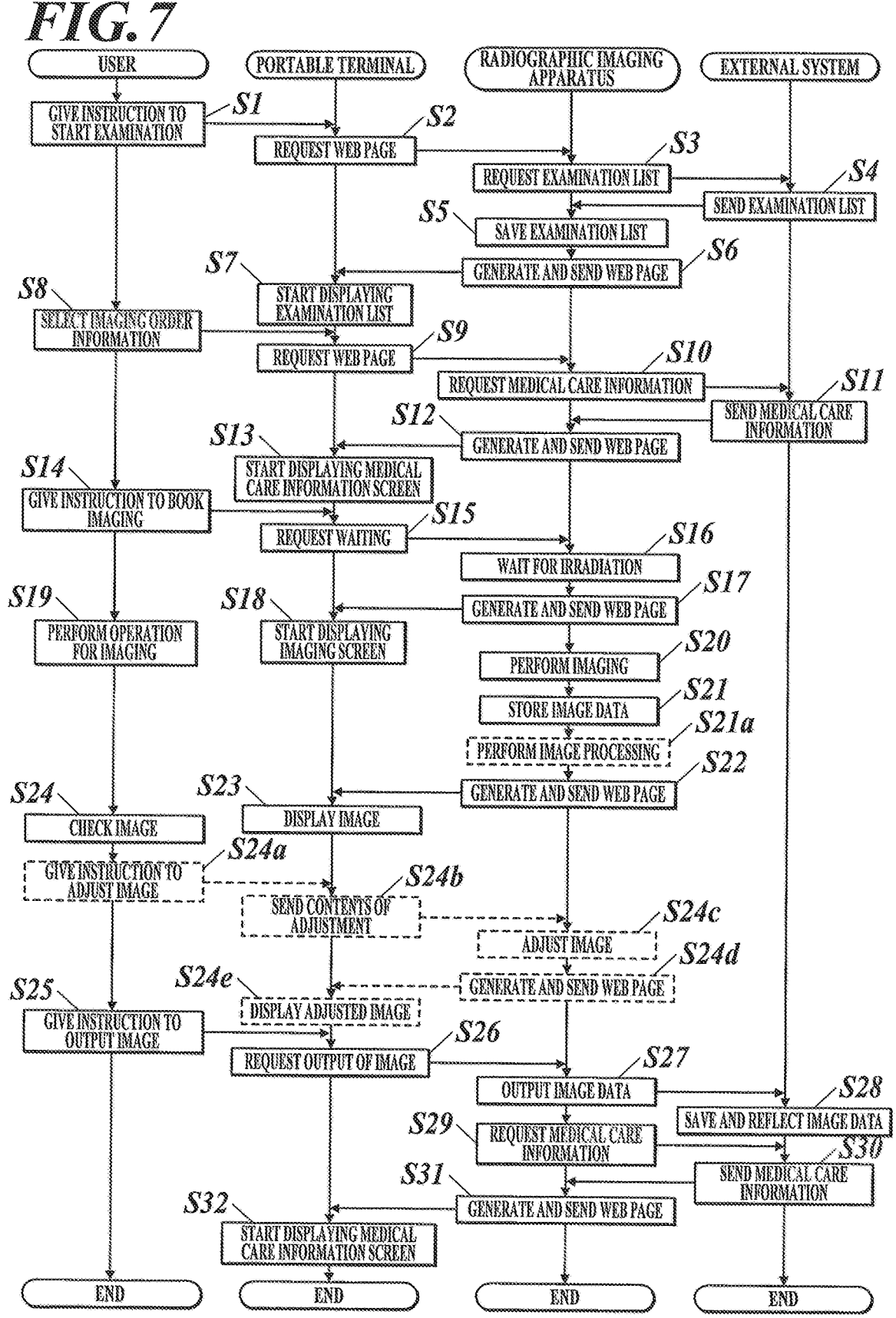
FIG. 7 is a ladder chart showing operation of the radiographic imaging system shown in FIG. 1.

Next, operation of the radiographic imaging system 100 is described. FIG. 7 is a ladder chart showing flow from radiographic imaging to display that are performed by the radiographic imaging system 100 of this embodiment.

As shown in FIG. 7, when a user gives an instruct to start an examination (Step S1), the portable terminal 3 sends a signal to request web content of an input screen of imaging order information to the radiographic imaging apparatus 2 (Step S2).

When receiving the signal, the radiographic imaging apparatus 2 sends a signal to request an examination list to the external system 4 (Step S3).

When receiving the signal, the external system 4 sends the examination list to the radiographic imaging apparatus 2 (Step S4).

When receiving the examination list, the radiographic imaging apparatus 2 saves the examination list (Step S5), and generates web content of the examination list and sends data thereof to the portable terminal 3 (Step S6).

When receiving the data, the portable terminal 3 displays a web page of the examination list (the list screen L shown in FIG. 5A) on the basis of the data (Step S7).

If the input screen is displayed by an application or the like installed in the portable terminal 3, after Step S1, in Step S2, the portable terminal 3 receives data of the examination list from the radiographic imaging apparatus 2, and in Step S7, the portable terminal 3 displays a web page thereof by the application on the basis of the data.

Thereafter, when the user selects imaging order information from the examination list (Step S8), the portable terminal 3 sends a signal to request web content of medical care information to the radiographic imaging apparatus 2 (Step S9).

When receiving the signal, the radiographic imaging apparatus 2 sends a signal to request the medical care information to the external system 4 (Step S10).

When receiving the signal, the external system 4 sends the medical care information to the radiographic imaging apparatus 2 (Step S11).

When receiving the medical care information, the radiographic imaging apparatus 2 generates the web content of the medical care information and sends data thereof to the portable terminal 3 (Step S12).

When receiving the data, the portable terminal 3 displays a web page of the medical care information (the medical care information screen I shown in FIG. 5B, etc.) on the basis of the data (Step S13).

Thereafter, when the user gives an instruction to book imaging (Step S14), the portable terminal 3 sends a signal to request waiting to the radiographic imaging apparatus 2 (Step S15).

When receiving the signal, the radiographic imaging apparatus 2 waits in such a way as to be able to perform imaging (Step S16), and generates web content of an imaging screen and sends data thereof to the portable terminal 3 (Step S17).

When receiving the data, the portable terminal 3 displays a web page of the imaging screen on the basis of the data (Step S18).

When the user confirms the patient name, the imaging order information and so forth displayed on the imaging screen, and performs an operation for imaging, namely, presses the exposure switch, while the radiographic imaging apparatus 2 is waiting (Step S19), the radiation emission apparatus 1 emits radiation to the patient (to the radiographic imaging apparatus 2), and the radiographic imaging apparatus 2 performs imaging (generates image data) (Step S20), and stores and links the image data with the medical care information in the storage 25 (Step S21). Then, the radiographic imaging apparatus 2 generates web content of a taken image on the basis of the image data and sends data thereof to the portable terminal 3 (Step S22).

When receiving the data of the web content, the portable terminal 3 displays a web page of the taken image on the basis of the data (Step S23).

If the radiographic imaging apparatus 2 has the image processing function, before or after Step S21, or in parallel with Step S21, the radiographic imaging apparatus 2 performs image processing (Step S21a).

Further, if the taken image is displayed by the application installed in the portable terminal 3 in Step S22, the radiographic imaging apparatus 2 sends the image data to the portable terminal 3 without generating the web content. Then, the portable terminal 3 stores the received image data, and in Step S23, generates the taken image on the basis of the image data and displays the same.

After Step S23, the user checks the taken image displayed on the portable terminal 3 (Step S24). Here, the user who has checked the processed image may judge that the image needs to be adjusted. In such a case, when the user gives an instruction to adjust the taken image by using the operation unit 35 of the portable terminal 3 (Step S24a), the portable terminal 3 sends contents of adjustment to be performed on the taken image to the radiographic imaging apparatus 2 (Step S24b). When receiving the updated parameter for the adjustment, the radiographic imaging apparatus 2 performs reprocessing (adjustment) on the image data (Step S24c). Then, the radiographic imaging apparatus 2 generates web content of an adjusted image on the basis of the adjusted image data obtained by the image adjustment and sends data thereof to the portable terminal 3 (Step S24d). Thereafter, the portable terminal 3 displays a web page of the adjusted image on the basis of the received data (Step S24e).

The image adjustment may be performed by the portable terminal 3.

When the user checks the adjusted image displayed on the portable terminal 3, judges that there is no problem, and gives an instruction to output image data thereof (Step S25), the portable terminal 3 sends a signal to request output of the image data to the radiographic imaging apparatus 2 (Step S26).

When receiving the signal, the radiographic imaging apparatus 2 outputs the image data to the external system 4 (Step S27).

When receiving the image data, the external system 4 saves the image data and also reflects the image data in the medical care information (Step S28).

After Step S27, the radiographic imaging apparatus 2 sends a signal to request the medical care information to the external system 4 (Step S29).

When receiving the signal, the external system 4 sends, to the radiographic imaging apparatus 2, the medical care information in which the currently taken image has been reflected (Step S30).

When receiving the medical care information, the radiographic imaging apparatus 2 generates web content of a medical care information screen and sends data thereof to the portable terminal 3 (Step S31).

When receiving the data, the portable terminal 3 displays a web page of the medical care information screen on the basis of the data (Step S32).

If the medical care information screen is displayed by the application installed in the portable terminal 3, at the end, the portable terminal 3 deletes the stored image data as needed.

As described above, the radiographic imaging apparatus 2 of the radiographic imaging system 100 of this embodiment includes: the radiation detector 22 including the substrate where the radiation detection elements are arranged two-dimensionally, the radiation detection elements generating amounts of electric charges corresponding to doses of radiation by being irradiated with the doses of the radiation; the reader 23 that reads the amounts of the electric charges generated by the respective radiation detection elements as signal values, and generates image data on the basis of the signal values; the first communication unit that communicates with the portable terminal 3 having a web browser; the second communication unit that receives external information from the external system 4; the storage 25 where the external information and the image data are stored; and the content generation unit that generates web content displayable on the web browser in response to a request from the portable terminal 3, wherein the first communication unit sends at least one of the web content, the image data and the external information to the portable terminal 3 in response to the request from the portable terminal 3.

Thus, the radiographic imaging apparatus 2 obtains the medical care information and/or the image(s) in the past examination(s) from the external system 4, and generates web content from the medical care information and the image data obtained by imaging performed this time. Hence, with a single terminal, various images can be checked without switching tabs of a browser or applications. As a result of that, a series of medical practice-related actions including imaging and image checking can be performed efficiently.

Second Embodiment

Next, a second embodiment of a radiograph display system (e.g. the radiographic imaging system in the first embodiment) of the present invention is described with reference to FIG. 8 to FIG. 13.

Figure 8:
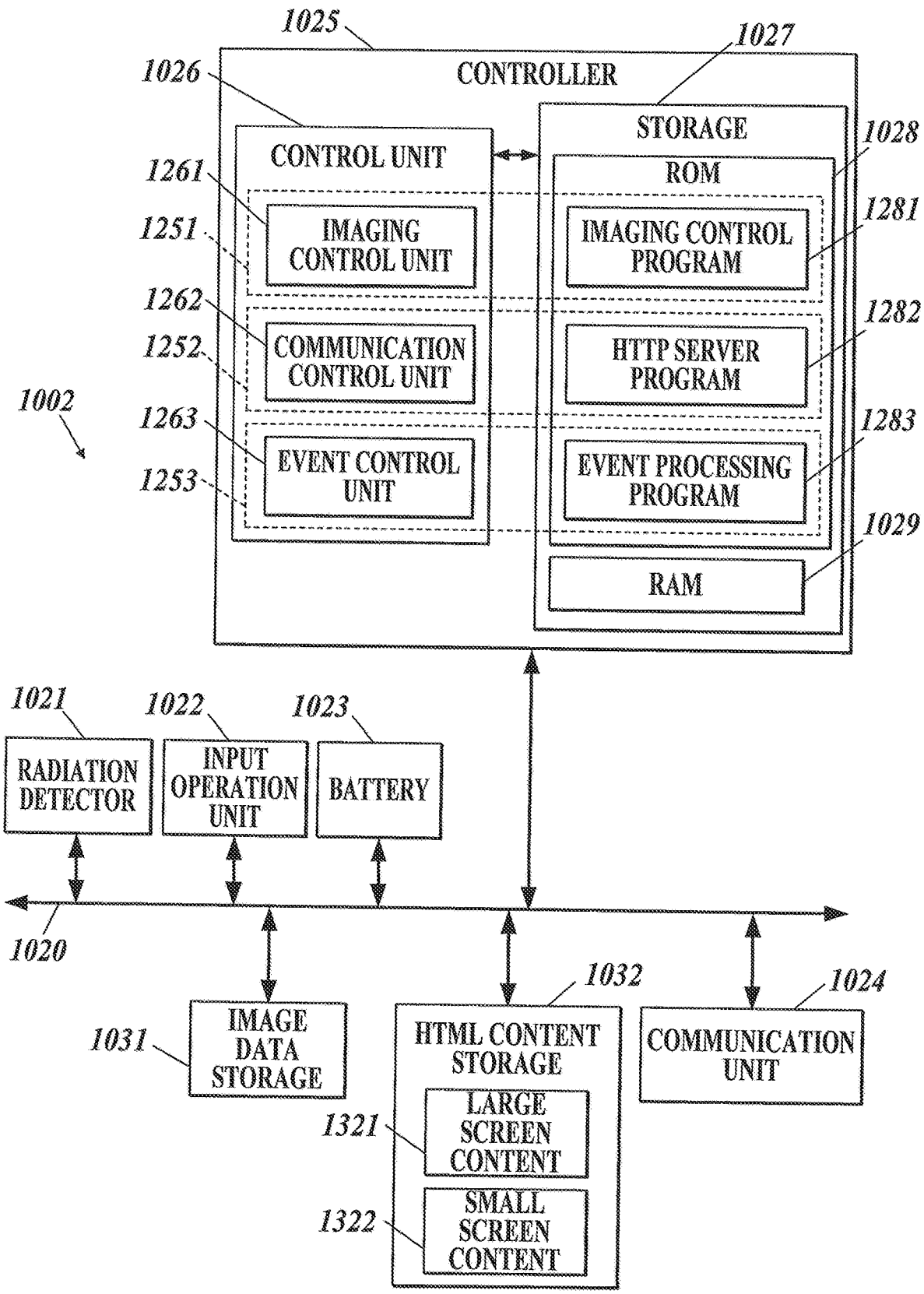
FIG. 8 is a block diagram showing main components of a radiographic imaging apparatus according to a second embodiment of the present invention.
Figure 9:
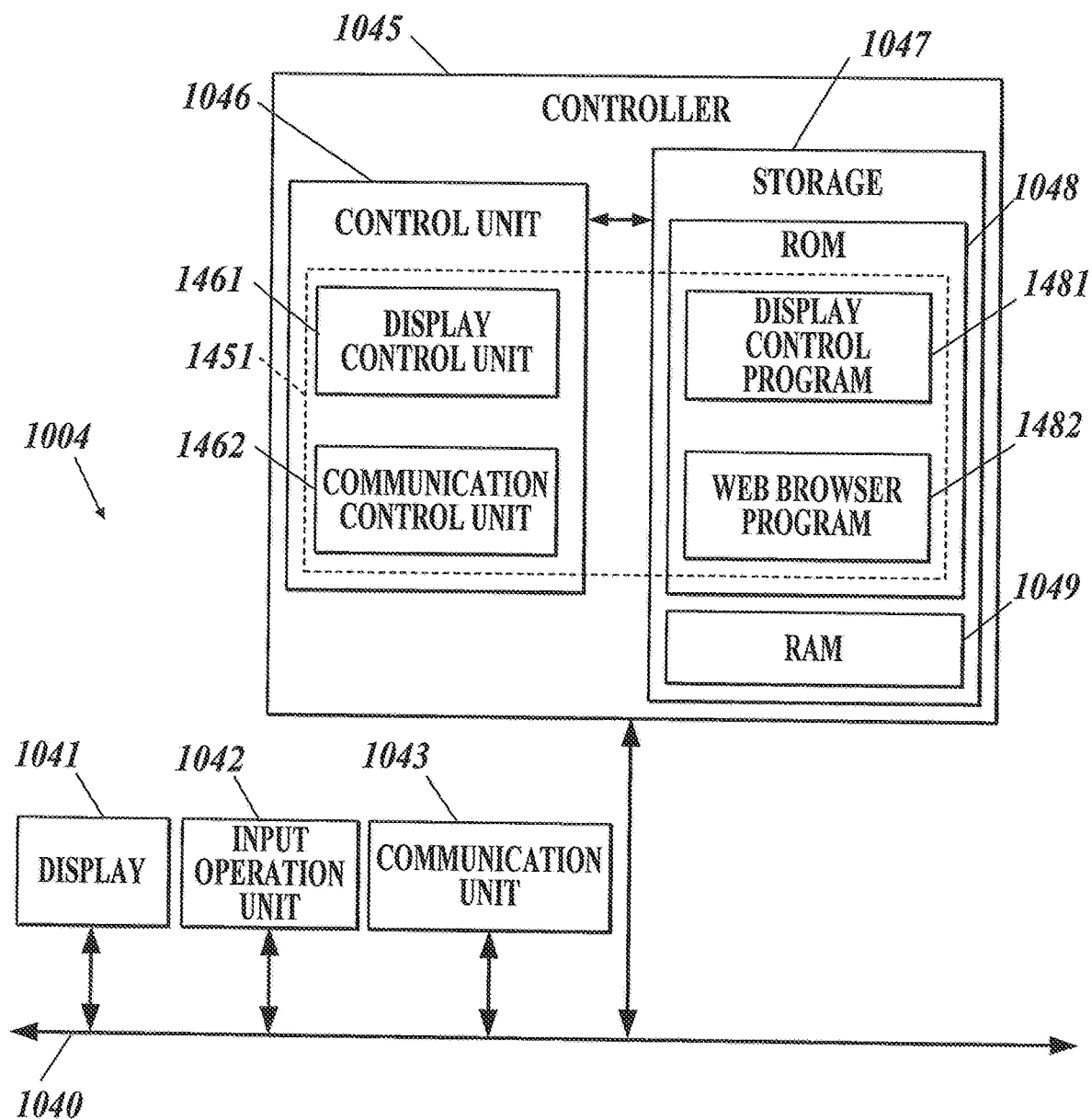
FIG. 9 is a block diagram showing main components of a terminal apparatus according to the second embodiment.

FIG. 8 is a block diagram showing main components of a radiographic imaging apparatus of this embodiment. FIG. 9 is a block diagram showing main components of a terminal apparatus of this embodiment.

Figure 10:
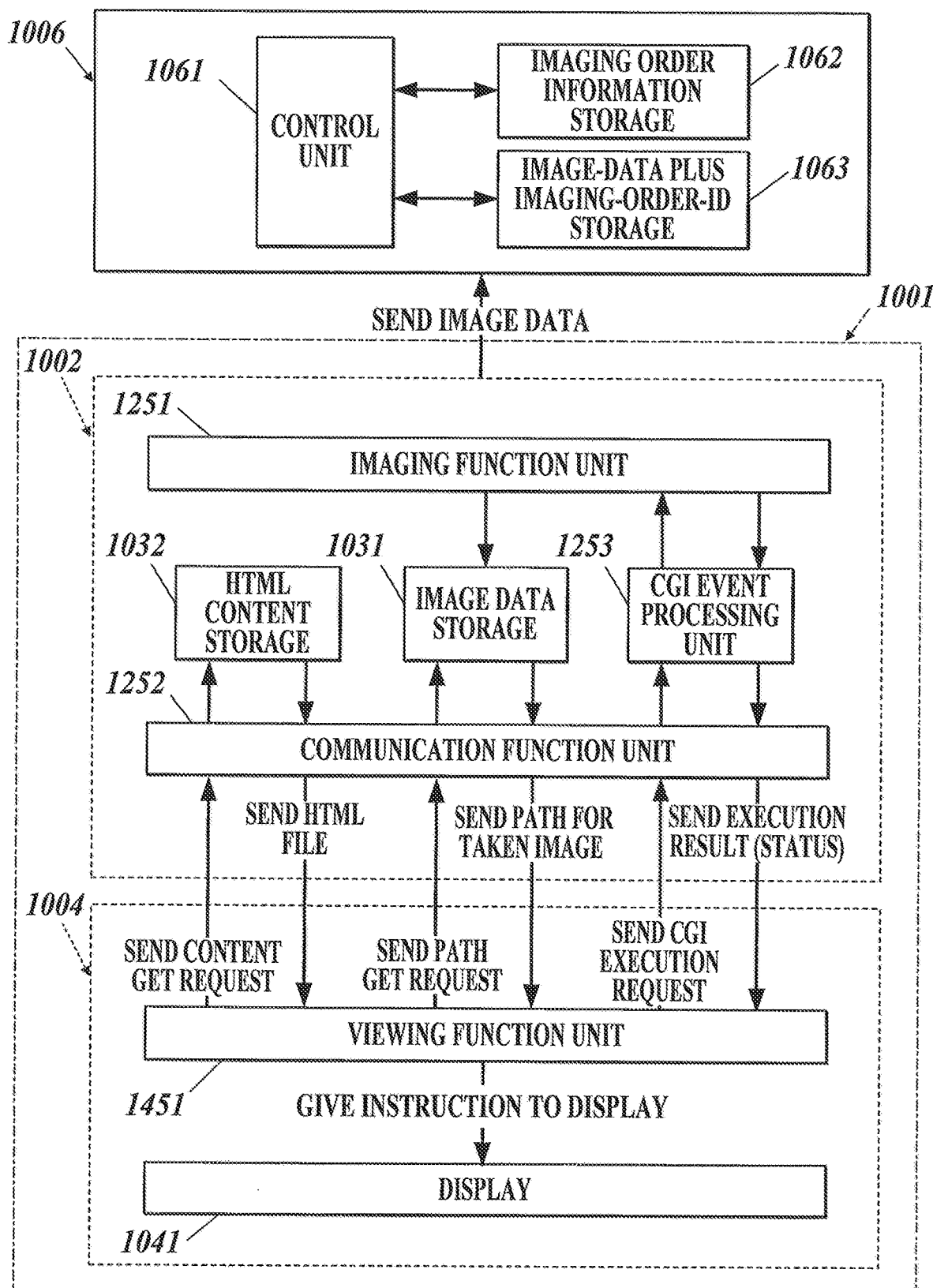
FIG. 10 is a schematic block diagram showing software configuration of an HTTP server function and a Web server function of a radiograph display system according to the second embodiment.

FIG. 10 is a schematic block diagram showing software configuration of an HTTP server function and a Web server function of a radiograph display system 1001 of this embodiment.

The radiograph display system 1001 (FIG. 10) of this embodiment includes: a portable radiographic imaging apparatus 1002 that performs radiographic imaging using a radiation detector 1021 (FIG. 8), thereby obtaining taken images; and a terminal apparatus 1004 (FIG. 9) that communicates with the radiographic imaging apparatus 1002, wherein the images taken by the radiographic imaging apparatus 1002 can be readily viewed on the terminal apparatus 1004.

[Radiographic Imaging Apparatus]

The radiographic imaging apparatus 1002 of this embodiment performs imaging by itself without tight control of a console 1006 (FIG. 10) that is a stationary control apparatus (computer) which controls the overall imaging operation.

As shown in FIG. 8, the radiographic imaging apparatus 1002 of this embodiment includes the radiation detector 1021, an input operation unit 1022, a battery 1023, a communication unit 1024, a controller 1025, an image data storage 1031 and an HTML content storage 1032.

The radiation detector 1021, the input operation unit 1022, the battery 1023, the communication unit 1024, the controller 1025, the image data storage 1031, the HTML content storage 1032 and other components of the radiographic imaging apparatus 1002 are connected to one another through a bus 1020 to send/receive various kinds of information to/from one another.

The radiographic imaging apparatus 1002 of this embodiment is portable, and performs radiographic imaging with the radiation detector 1021 shown in FIG. 8, thereby obtaining taken images. The radiographic imaging apparatus 1002 is, for example, what is called, a flat panel detector (FPD) where solid imaging elements are arranged two-dimensionally.

As described below, the radiographic imaging apparatus 1002 sends/receives data and so forth to/from various types of terminal apparatus 1004 wirelessly. Further, the radiographic imaging apparatus 1002 has the built-in battery 1023 to be used smoothly without a cable.

Thus, the radiographic imaging apparatus 1002 of this embodiment is portable, and hence can perform imaging with a high degree of freedom, such as portable imaging at bedside of a patient, to suit the condition of a patient.

The radiation detector 1021 detects, under control of the controller 1025, radiation emitted from a not-shown radiation source and passed through a subject.

Specific configuration of the radiation detector 1021 is not particularly limited, and for example, there can be used a direct type that directly converts radiation energy into electric charges using photoconductive substances, such as a-Se, as radiation detection elements, and reads the electric charges as electric signals in pixel units with two-dimensionally arranged switching elements for signal reading, such as TFTs (Thin Film Transistors); or an indirect type that converts radiation energy into light with a scintillator or the like, converts the light into electric charges with two-dimensionally arranged photoelectric conversion elements, such as photodiodes, and reads the electric charges as electric signals with TFTs or the like.

The input operation unit 1022 is for a user to perform input operations, and is constituted of, for example, a power switch to turn on a power source of the radiographic imaging apparatus 1002.

The battery 1023 supplies power to the components of the radiographic imaging apparatus 1002.

The built-in battery 1023 being the source of power supply of the radiographic imaging apparatus 1002 enables imaging with a high degree of freedom without cable connection.

The battery 1023 of this embodiment may be either a replaceable primary battery or a chargeable secondary battery (storage battery).

The remaining battery level of the battery 1023 is grasped by the below-described controller 1025, and notified, in response to a request from a viewing function unit 1451 of the below-described terminal apparatus 1004, to the terminal apparatus 1004 as fluctuant information that changes with time.

The communication unit 1024 sends/receives data and so forth to/from various types of terminal apparatus 1004 wirelessly, and includes a not-shown antenna.

The communication unit 1024 operates under control of a communication control unit 1262.

The controller 1025 controls the overall operation of the radiographic imaging apparatus 1002.

As shown in FIG. 8, the controller 1025 includes: a control unit 1026 that includes a CPU (Central Processing Unit) or the like; and a storage 1027 that includes a ROM (Read Only Memory) 1028 and a RAM (Random Access Memory) 1029.

The control unit 1026 includes an imaging control unit 1261 that controls imaging operation of the radiographic imaging apparatus 1002, the communication control unit 1262 that controls operation of the communication unit 1024 to communicate with external apparatuses, and an event control unit that performs event processing when requested via Web.

The ROM 1028 stores therein: various process programs that are executed by the control unit 1026; and so forth. In this embodiment, the ROM 1028 stores therein an imaging control program 1281, an HTTP server program 1282, an event processing program 1283 and so forth.

The RAM 1029 temporarily stores therein data and so forth necessary for various processes.

In this embodiment, an imaging process is realized by the imaging control unit 1261 in cooperation with the imaging control program 1281. The imaging control unit 1261 and the imaging control program 1281 read thereby constitute an imaging function unit 1251 (FIG. 10).

As shown in FIG. 10, the imaging function unit 1251 stores, in the image data storage 1031, image data of taken images obtained by the radiation detector 1021 performing imaging.

More specifically, when receiving an imaging order, thereby performing imaging, the imaging function unit 1251 attaches unique identification information (hereinafter called an image ID) to image data of a taken image obtained by the imaging, and stores the image data of the taken image with the image ID attached in the image data storage 1031.

A communication process is realized by the communication control unit 1262 in cooperation with the HTTP server program 1282. The communication control unit 1262 and the HTTP server program 1282 read thereby constitute a communication function unit 1252 (FIG. 10).

The communication function unit 1252 of this embodiment functions as a providing unit that provides the terminal apparatus 1004 with, by the Web server function, viewing information to view the taken image(s) based on the data (the image data of the taken image) stored in the below-described image data storage 1031.

The viewing information in this embodiment is a Path (folder path) indicating a location where the image data of the taken image, which is stored in the HTML content storage 1032, is stored.

In this embodiment, in response to a request, such as a content GET request (request for content), from the viewing function unit 1451 (FIG. 10) of the terminal apparatus 1004 having the below-described Web browser function, an HTML file (HTML content) or the like that meets the request is provided.

An event execution process is realized by the event control unit 1263 in cooperation with the event processing program 1283. The event control unit 1263 and the event processing program 1283 read thereby constitute a CGI event processing unit 1253 (FIG. 10).

The image data storage 1031 stores therein, for example, the taken images (radiographs) obtained by the radiation detector 1021 as data, and is constituted of, for example, an SSD (Solid State Drive).

As described above, the image data of the taken images stored in the image data storage 1031 are correlated and stored therein with their respective unique identification information (image IDs).

The image data stored in the image data storage 1031 are, as shown in FIG. 10, sent to the stationary control apparatus (in this embodiment, the console 1006) installed, for example, in a consultation room, by the radiographic imaging apparatus 1002 being connected to the control apparatus (the console 1006). After the image data are sent, the data are successively deleted from the image data storage 1031.

The image data storage 1031 does not need to be a storage built in the radiographic imaging apparatus 1002, and for example, may be a storage attachable/detachable to/from the radiographic imaging apparatus 1002, such as a USB (Universal Serial Bus) memory or an SD (Secure Digital) memory Card®.

The HTML content storage 1032 stores therein HTML files (HTML contents) to be provided in response to content GET requests from the viewing function unit 1451 (FIG. 9 and FIG. 10) of the below-described terminal apparatus 1004.

Each HTML file contains, for example, screen layout information for the terminal apparatus 1004 to display, on a display 1041, information which the radiographic imaging apparatus 1002 has. The viewing function unit 1451 analyzes the HTML file, thereby constructing a viewing screen on the display screen of the display 1041 of the terminal apparatus 1004 on the basis of the screen layout information.

In this embodiment, the HTML content storage 1032 stores therein, as the screen layout information, large screen content (content for a large screen(s)) 1321 to construct layout suitable for a large screen and small screen content (content for a small screen(s)) 1322 to construct layout suitable for a small screen. The screen layout information stored in the HTML content storage 1032 is not limited to those described here, and hence three or more types of the screen layout information for more specific screen sizes and/or resolutions may be stored therein.

In the HTML file, the Path (folder path) is described, the Pass indicating a location where the image data of the taken image which the radiographic imaging apparatus 1002 has is stored. By getting the Path, the viewing function unit 1451 having the Web browser function can display, on the display screen of the display 1041, the taken image based on the image data stored in the image data storage 1031 of the radiographic imaging apparatus 1002.

If requested by the viewing function unit 1451, the image data of the taken image is provided for the viewing function unit 1451, the image data being converted into a general format, such as BMP, JPEG or PNG, displayable/interpretable by the Web browser function. Timing at which the image data of the taken image is converted into the general format is not particularly limited. For example, the image data may be prepared by being converted into the general format in advance, or may be converted into the general format when the viewing function unit 1451 requests the taken image for viewing from the communication function unit 1252 of the radiographic imaging apparatus 1002.

In the image data storage 1031, as the image data of the taken image to be provided for the viewing function unit 1451, a thumbnail image that is displayed at the time of displaying a list of taken images (hereinafter called a taken image list) and a detailed image that is displayed in a detail check screen are separately stored, and different Paths (folder paths) may be assigned thereto.

Thus, separate storage of the thumbnail image(s) and the detailed image(s) can increase responsiveness to a request(s) sent from the viewing function unit 1451.

The information displayed on the viewing screen contains the fluctuant information that cannot be described in a fixed manner. The fluctuant information is information that changes with time, and in this embodiment, for example, the information on the remaining battery level of the battery 1023.

In the HTML file, a name of a CGI script file is described at a point where display based on the fluctuant information should be done.

Embedding the CGI script file in the HTML file allows the CGI event processing unit 1253 to generate, in response to a CGI execution request from the viewing function unit 1451, a partial script of the HTML to be dynamic according to the status (e.g. the remaining battery level of the battery 1023 in this embodiment) at the time, and sends the same as a response to the viewing function unit 1451. This can display, at the fluctuant information point, content corresponding to the latest status.

[Terminal Apparatus]

The terminal apparatus 1004 of this embodiment is a small apparatus that is easy to carry, such as a portable terminal apparatus exemplified by a smartphone, a laptop personal computer (hereinafter a personal computer is referred to as a PC), or a tablet PC.

In this embodiment, it is assumed that the terminal apparatus 1004 is a laptop PC that includes the display 1041 having a relatively large display screen, or a portable terminal apparatus that includes the display 1041 having a relatively small display screen.

As shown in FIG. 9, the terminal apparatus 1004 includes the display 1041, an input operation unit 1042, a communication unit 1043 and a controller 1045.

The display 1041, the input operation unit 1042, the communication unit 1043, the controller 1045 and other components of the terminal apparatus 1004 are connected to one another through a bus 1040 to send/receive various kinds of information to/from one another.

The display 1041 performs display on the basis of various data.

In this embodiment, the display 1041 displays: image data, such as the taken images obtained by the radiographic imaging apparatus 1002 performing imaging, and thumbnail images of the taken images; the display screen based on content (i.e. the large screen content 1321 or the small screen content 1322 shown in FIG. 8), which constitutes the display screen, stored in the HTML content storage 1032 of the radiographic imaging apparatus 1002; other various images; and so forth.

The display 1041 displays various kinds of display screen under control of a display control unit 1461.

On the display screen of the display 1041 of this embodiment, a touchscreen constituting the input operation unit 1042 is placed, so that various input operations can be performed by operating the touchscreen.

Figure 11:
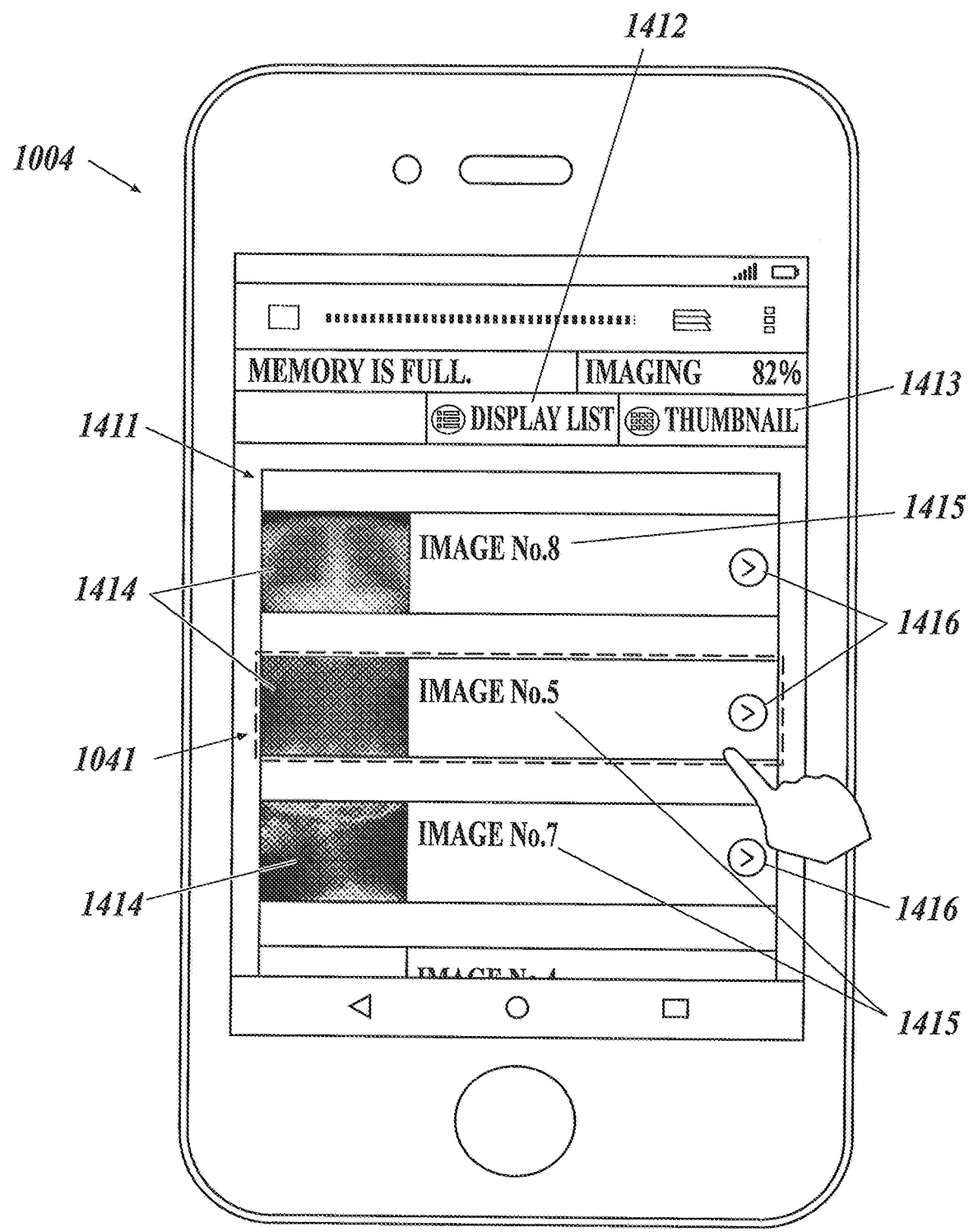
FIG. 11 shows an example of a display screen in a taken image display process.
Figure 12:
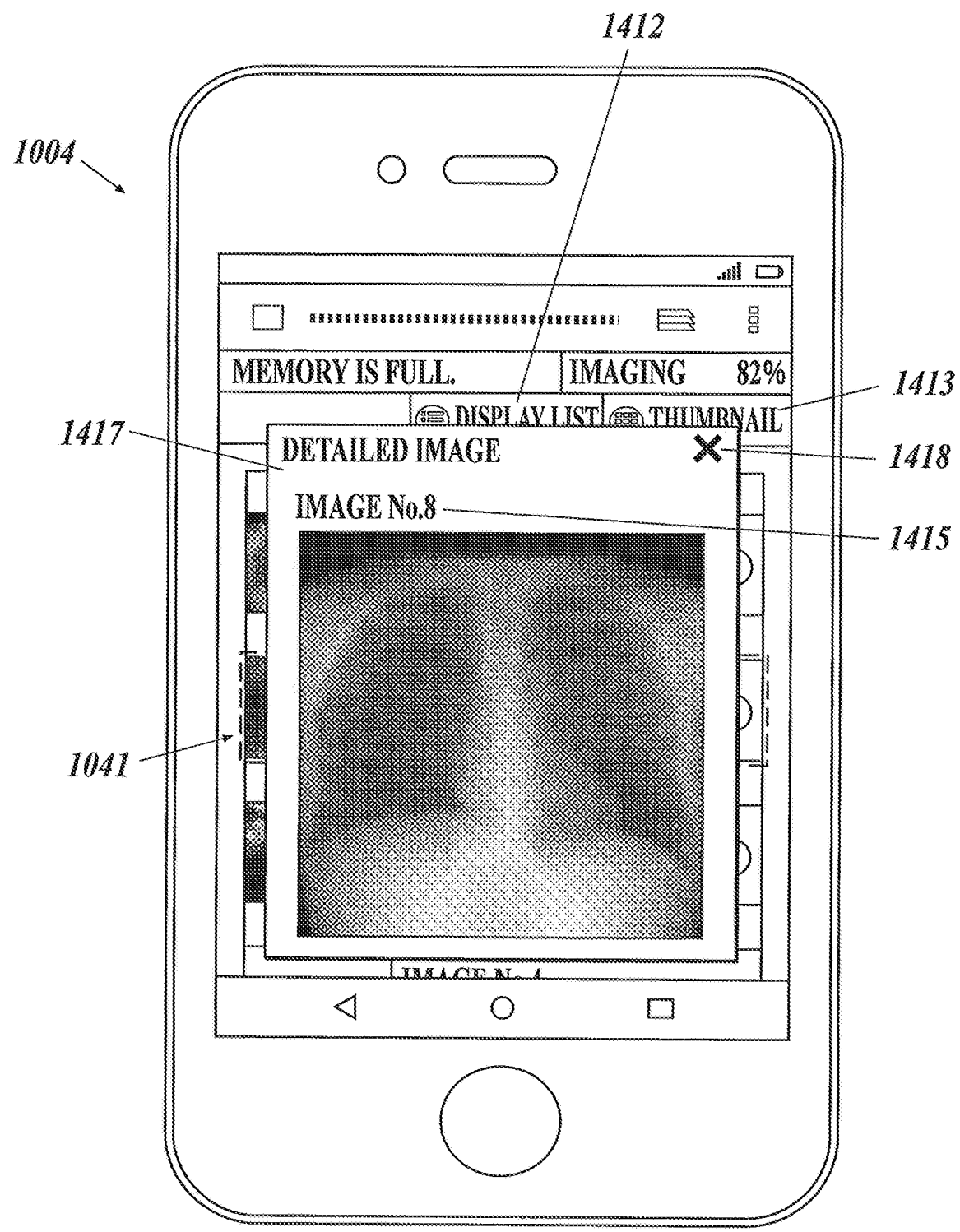
FIG. 12 shows an example of the display screen in the taken image display process.

FIG. 11 and FIG. 12 show examples of the display screen of the display 1041 of the terminal apparatus 1004 of this embodiment. FIG. 11 shows a list display screen 1411 of the taken images provided by the radiographic imaging apparatus 1002 displayed on the display 1041. FIG. 12 shows a detailed image display screen 1417 of one of the taken images provided by the radiographic imaging apparatus 1002 displayed on the display 1041.

As shown in FIG. 11, the list display screen 1411 of this embodiment is provided with: a list display button 1412; and a thumbnail display button 1413 to display thumbnail images. FIG. 11 shows the state in which the taken image list is displayed.

In the taken image list displayed in the list display screen 1411, sets constituted of thumbnail images 1414 of the taken images and their respective image IDs 1415 are displayed together with detail buttons 1416 to display detailed image display screens 1417 corresponding to the respective thumbnail images 1414.

When a user touches one of the detail buttons 1416, a detailed image display screen 1417 corresponding to a thumbnail image 1414 at a point corresponding to the touch operation is displayed.

FIG. 12 shows the detailed image display screen 1417 of the taken image with the image ID "Image No. 8" attached. The detailed image display screen 1417 is provided with a close button 1418. When a user touches the close button 1418, the detailed image display screen 1417 is closed, and the previously displayed list display screen 1411 is displayed again.

The input operation unit 1042 is for a user to perform input operations, and is constituted of, for example, the above touchscreen integrated with the display 1041 or a keyboard including various keys. The input operation unit 1042 is not limited to one physically integrated with the terminal apparatus 1004, and hence may be a device, such as a mouse, connected to the terminal apparatus 1004 by a wired system or any type of wireless system.

The communication unit 1043 sends/receives data to/from the radiographic imaging apparatus 1002 and so forth wirelessly, and includes a not-shown antenna.

The communication unit 1043 operates under control of a communication control unit 1462.

The controller 1045 controls the overall operation of the terminal apparatus 1004.

As shown in FIG. 9, the controller 1045 includes: a control unit 1046 that includes a CPU (Central Processing Unit) or the like; and a storage 1047 that includes a ROM (Read Only Memory) 1048 and a RAM (Random Access Memory) 1049.

The control unit 1046 includes the display control unit 1461 that controls the display 1041 of the terminal apparatus 1004, and the communication control unit 1462 that controls operation of the communication unit 1043 to communicate with external apparatuses.

The ROM 1048 stores therein: various process programs that are executed by the display control unit 1461 and the communication control unit 1462; and so forth. In this embodiment, the ROM 1048 stores therein a display control program 1481, a Web browser program 1482 and so forth.

The RAM 1049 temporarily stores therein data and so forth necessary for various processes.

In this embodiment, a viewing process is realized by the display control unit 1461 and the communication control unit 1462 in cooperation with the display control program 1481 and the Web browser program 1482. The display control unit 1461 and the communication control unit 1462 and the display control program 1481 and the Web browser program 1482 read thereby constitute the viewing function unit 1451 (FIG. 10).

The viewing function unit 1451 has the Web browser function, and as shown in FIG. 10, communicates with the communication function unit 1252, which is the providing unit of the radiographic imaging apparatus 1002 having the Web server function, and gets a Path (folder path), which is the viewing information, from the radiographic imaging apparatus 1002, and displays a taken image(s) on the display 1041 on the basis of the Path (folder path).

The viewing function unit 1451 of this embodiment requests the communication function unit 1252 of the radiographic imaging apparatus 1002 to send content (a content GET request), and when receiving an HTML file (HTML content) or the like as a response, instructs the display 1041 to perform display on the basis of the HTML file.

In this embodiment, the viewing function unit 1451 requests the communication function unit 1252 to execute a CGI (a CGI execution request), and when receiving the status for the fluctuant information point in the HTML content, reflects the received status on the display screen of the display 1041.

[Operation of Radiograph Display System]

Next, operation of the radiograph display system 1001 is described with reference to FIG. 13 and so forth.

Figure 13:
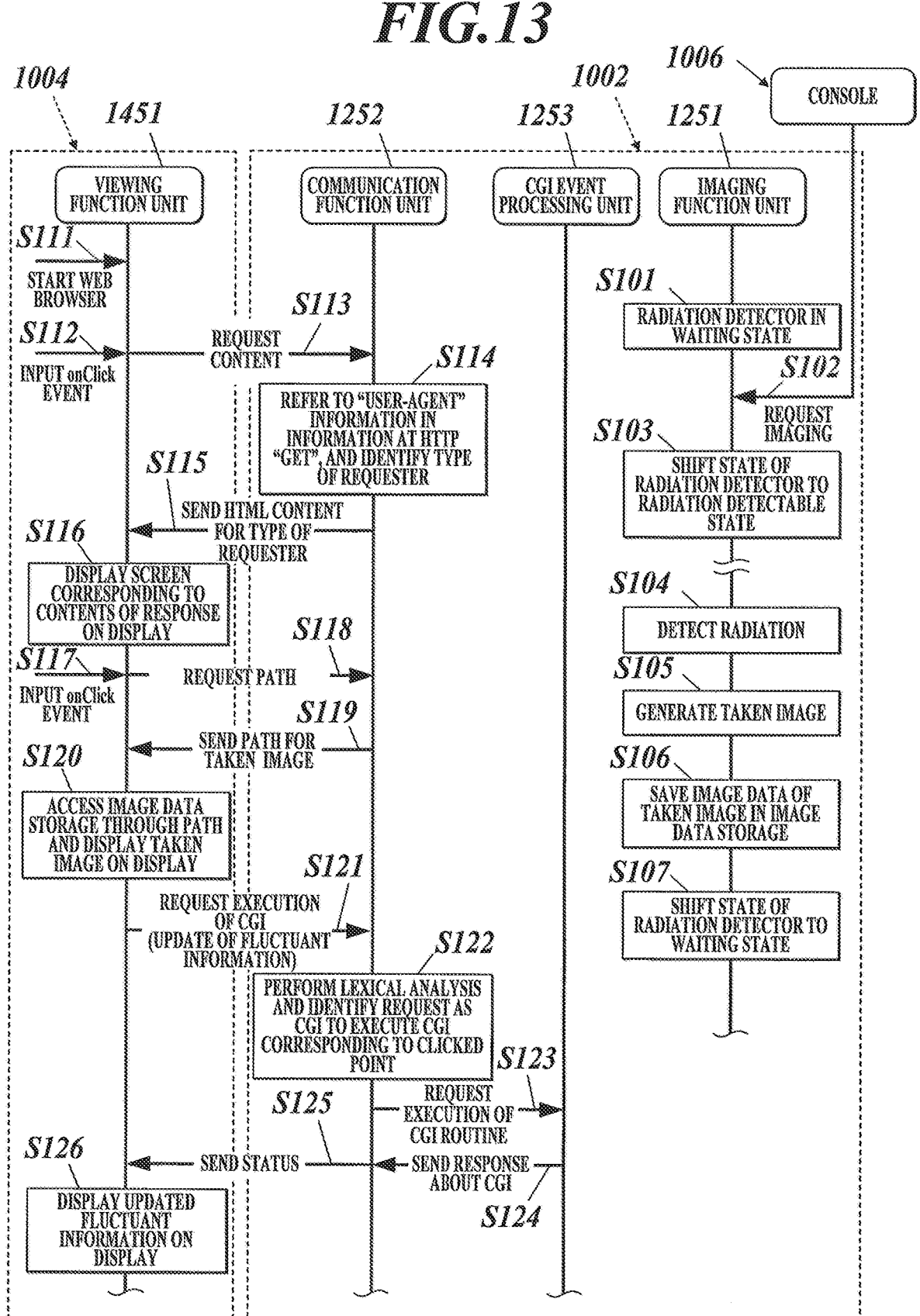
FIG. 13 is a sequence diagram showing a radiograph display process according to the second embodiment.

As shown in FIG. 13, the imaging function unit 1251 of the radiographic imaging apparatus 1002 of this embodiment leaves the radiation detector 1021 in a waiting state until receiving an imaging execution request (imaging order) from the console 1006 (Step S101). Until then, even if the radiation detector 1021 is irradiated, the radiation detector 1021 does not react to this and keeps the state, in which no radiation detection is performed.

When imaging is performed, a control unit 1061 of the console 1006 requests the imaging function unit 1251 to perform imaging (an imaging execution request(s)) (Step S102). The imaging execution request is made as described below.

That is, as shown in FIG. 10, the console 1006 includes an imaging order information storage 1062 where imaging order information is stored. The control unit 1061 of the console 1006 successively inputs imaging orders of the imaging order information stored in the imaging order information storage 1062 to the radiographic imaging apparatus 1002. At the time, the control unit 1061 attaches unique imaging order IDs to the respective imaging orders.

When receiving the imaging order information (an imaging order) from the console 1006, the imaging function unit 1251 shifts the state of the radiation detector 1021 to a radiation detectable state (Step S103).

When irradiated with radiation emitted from a not-shown radiation source, the radiation detector 1021 detects the radiation that has passed through an imaging site of a patient as a subject (Step S104), and generates a taken image (Step S105).

The imaging function unit 1251 attaches a unique image ID to image data of the generated taken image and saves the same in the image data storage 1031 (Step S106), and puts the radiation detector 1021 in the waiting state again (Step S107). Further, the imaging function unit 1251 sends the image data of the taken image with the image ID attached to the console 1006.

When receiving the image data of the taken image from the radiographic imaging apparatus 1002, the console 1006 correlates the imaging order ID, which has been attached to the imaging order at the time of the imaging, with the image data of the taken image and stores the same in an image-data plus imaging-order-ID storage 1063.

After sending the image data of the taken image to the console 1006, the imaging function unit 1251 deletes the image data of the taken image from the image data storage 1031 of the radiographic imaging apparatus 1002.

In this embodiment, when a radiograph display process to view taken images or the like on the portable terminal 1004 is performed, first, a Web browser of the terminal apparatus 1004 is started (Step S111).

Then, in order to display a viewing screen to view taken images or the like, a user inputs an onClick event through the input operation unit 1042, such as a touchscreen (Step S112). The viewing function unit 1451 having the Web browser function analyzes contents of an event, which has been input on the basis of the form or the like of the operation to the input operation unit 1042, and if the event is a request for the viewing screen (main screen), sends a content GET request ("HTTP "GET"", i.e. a request for the viewing screen (main screen)) to the communication function unit 1252 of the radiographic imaging apparatus 1002 (Step S113). When receiving the content GET request from the viewing function unit 1451, the communication function unit 1252 having the Web server function refers to "User-Agent" information in information at "HTTP "GET"", and identifies the type (screen size, resolution, etc.) of the requester (Step S114), and on the basis of the identification result, sends an HTML file (HTML content) for the type (screen size, resolution, etc.) of the requester to the viewing function unit 1451 of the terminal apparatus 1004 (Step S115).

That is, when determining from the "User-Agent" information that the requester of the content GET request is a tablet PC having a large screen, the communication function unit 1252 sends the large screen content 1321 as a response, whereas when determining therefrom that the requester of the content GET request is a portable terminal apparatus having a small screen, the communication function unit 1252 sends the small screen content 1322 as a response.

When getting the HTML file (HTML content) from the communication function unit 1252, the viewing function unit 1451 analyzes the HTML file and reads the screen layout information contained in the HTML file, and constructs the viewing screen on the display screen of the display 1041 of the terminal apparatus 1004 on the basis of the screen layout information. That is, the viewing function unit 1451 displays a screen corresponding to contents of the response on the display 1041 (Step S116). This can display, for example, the screen shown in FIG. 11 if the terminal apparatus 1004 is a portable terminal apparatus, the display 1041 of which has a small screen.

Thus, sending, to a terminal apparatus 1004, an HTML file (HTML content) containing the screen layout information suitable for the type of the terminal apparatus 1004 can provide any terminal apparatus 1004 with the display screen that is easy-to-use in the terminal apparatus 1004.

If the user desires to display a taken image or the like on the display 1041, he/she inputs an onClick event through the input operation unit 1042, such as a touchscreen (Step S117). The viewing function unit 1451 analyzes contents of an event, which has been input on the basis of the form or the like of the operation to the input operation unit 1042, and if the event is a request for a taken image (e.g. if the user touches one of the detail buttons 1416), sends a Path GET request ("HTTP "GET"", i.e. a request for a Path) for the taken image to the communication function unit 1252 (Step S118).

When receiving the Path GET request from the viewing function unit 1451, the communication function unit 1252 sends a Path for the taken image to the viewing function unit 1451 of the terminal apparatus 1004 (Step S119).

When receiving the Path from the communication function unit 1252, the viewing function unit 1451 access the image data storage 1031 of the radiographic imaging apparatus 1002 through the Path, and displays the taken image (e.g. the detailed image shown in FIG. 12) on the display screen of the display 1041 (Step S120).

If a CGI script file is embedded in the HTML file (HTML content) sent from the communication function unit 1252 to the viewing function unit 1451 of the terminal apparatus 1004 in response to, for example, the request for the viewing screen (main screen), the viewing function unit 1451 sends a CGI execution request (a fluctuant information update request) to the communication function unit 1252 (Step S121).

The communication function unit 1252 performs lexical analysis on contents of the request sent from the viewing function unit 1451, and, when identifying the request as a CGI requesting update of the fluctuant information (Step S122), requests the CGI event processing unit 1253 to execute a CGI routine (Step S123).

When requested to execute the CGI routine, the CGI event processing unit 1253 generates a partial script of the HTML to be dynamic according to the status at the time, and sends the same to the communication function unit 1252 (Step S124).

The communication function unit 1252 sends, to the viewing function unit 1451, the status sent from the CGI event processing unit 1253 (Step S125).

This can display a status display screen with contents corresponding to the latest status fitted to the fluctuant information point (e.g. the point where the remaining battery level of the battery 1023 is displayed) on the display 1041 (Step S126).

[Effects of Radiograph Display System]

A conventional radiograph display system is used on the assumption that dedicated software has been installed in a terminal apparatus. Hence, it is difficult to readily use a portable terminal apparatus (a smartphone, etc.) at hand for the system.

Further, the terminal apparatus in the conventional system obtains IDs of taken images only. The terminal apparatus therein is not expected to be used as a monitor to check taken images at the imaging location.

Hence, in order to check taken images, a user needs to go to a console. Thus, the conventional radiograph display system cannot satisfy a desire to check taken images readily and immediately after imaging.

Then, the radiograph display system of this embodiment includes: the radiographic imaging apparatus 1002 including the image data storage 1031 where taken images are stored as data, and the communication function unit 1252 as the providing unit that provides the terminal apparatus 1004 with, by the Web server function, the viewing information to view the taken images based on the data stored in the image data storage 1031; and the terminal apparatus 1004 including the display 1041 that performs display on the basis of various data, and the viewing function unit 1451 that communicates with the communication function unit 1252 to obtain the viewing information from the radiographic imaging apparatus 1002, and displays the taken images on the display 1041 on the basis of the viewing information.

This allows a user to readily view and check, for example, images taken by the radiographic imaging apparatus 1002 with the terminal apparatus 1004 at hand. Accordingly, a user can readily and immediately judge whether re-imaging is necessary or not and make diagnosis of a diseased part(s) using a taken image(s), for example.

Further, in order to allow the terminal apparatus 1004 to display taken images, the radiographic imaging apparatus 1002 sends only Paths, which identify locations of files, to the terminal apparatus 1004, and does not send image data itself. This makes data to be sent/received light, and allows a user to immediately view taken images even under a relatively weak communication environment.

Further, thanks to the Web browser function, the image data stored in the image data storage 1031 of the radiographic imaging apparatus 1002 can be viewed with the terminal apparatus 1004, but the terminal apparatus 1004 does not manage or keep the image data of the taken images and the imaging order information. Hence, even if the terminal apparatus 1004 is damaged, broken or the like, there is no risk of losing the image data of the taken images, the imaging order information, the image IDs, which correlates the image data of the taken images with the imaging order information, and so forth.

Further, these data and information are highly private. The present invention does not import these data and information into a memory of the portable terminal apparatus 1004, which can be easily taken out, and accordingly contributes to protection of personal information.

Third Embodiment

Next, a third embodiment of the radiograph display system of the present invention is described with reference to FIG. 14 to FIG. 17.

The third embodiment is different from the second embodiment mainly in function and role of the terminal apparatus 1004 and the radiographic imaging apparatus 1002. Hereinafter, the points different from the second embodiment are described mainly.

Figure 14:
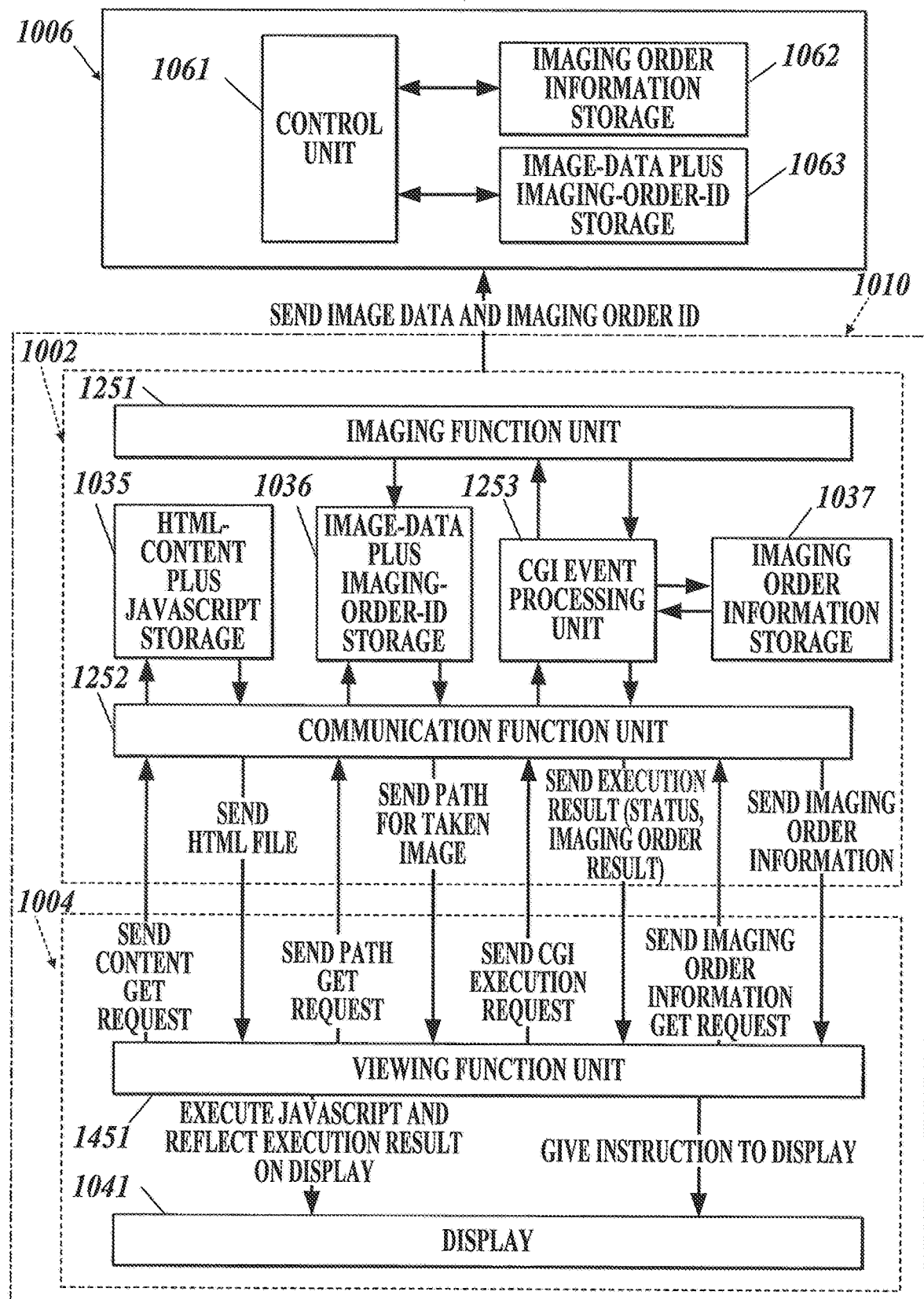
FIG. 14 is a schematic block diagram showing software configuration of an HTTP server function and a Web server function of a radiograph display system according to a third embodiment of the present invention.

FIG. 14 is a schematic block diagram showing software configuration of an HTTP server function and a Web server function of a radiograph display system 1010 of this embodiment.

As shown in FIG. 14, in this embodiment, the radiographic imaging apparatus 1002 includes an imaging order information storage 1037 which stores therein imaging order information (patient name(s), imaging site(s), etc.) on imaging in the form to be providable for the terminal apparatus 1004.

The imaging order information is stored in the imaging order information storage 1037 in advance by being sent from the console 1006 or the like to the radiographic imaging apparatus 1002.

In this embodiment, each HTML content is stored in an HTML-content plus JavaScript storage 1035 of the radiographic imaging apparatus 1002 such that a program language, such as JavaScript®, is embedded in the HTML content.

Hence, when the viewing function unit 1451 of the terminal apparatus 1004 having the Web browser function sends a request for HTML content (i.e. an HTML content GET request) to the communication function unit 1252 of the radiographic imaging apparatus 1002 having the Web server function as with the second embodiment, the radiographic imaging apparatus 1002 sends the HTML content with JavaScript® embedded to the terminal apparatus 1004.

The HTML content sent from the radiographic imaging apparatus 1002 to the terminal apparatus 1004 in response to the HTML content GET request sent from the terminal apparatus 1004 to the radiographic imaging apparatus 1002 contains a CGI execution request for displaying the imaging order information, which the radiographic imaging apparatus 1002 currently has, on the display 1041 of the terminal apparatus 1004.

Hence, in this embodiment, the imaging order information can be viewed on the display 1041 of the terminal apparatus 1004.

Figure 15:
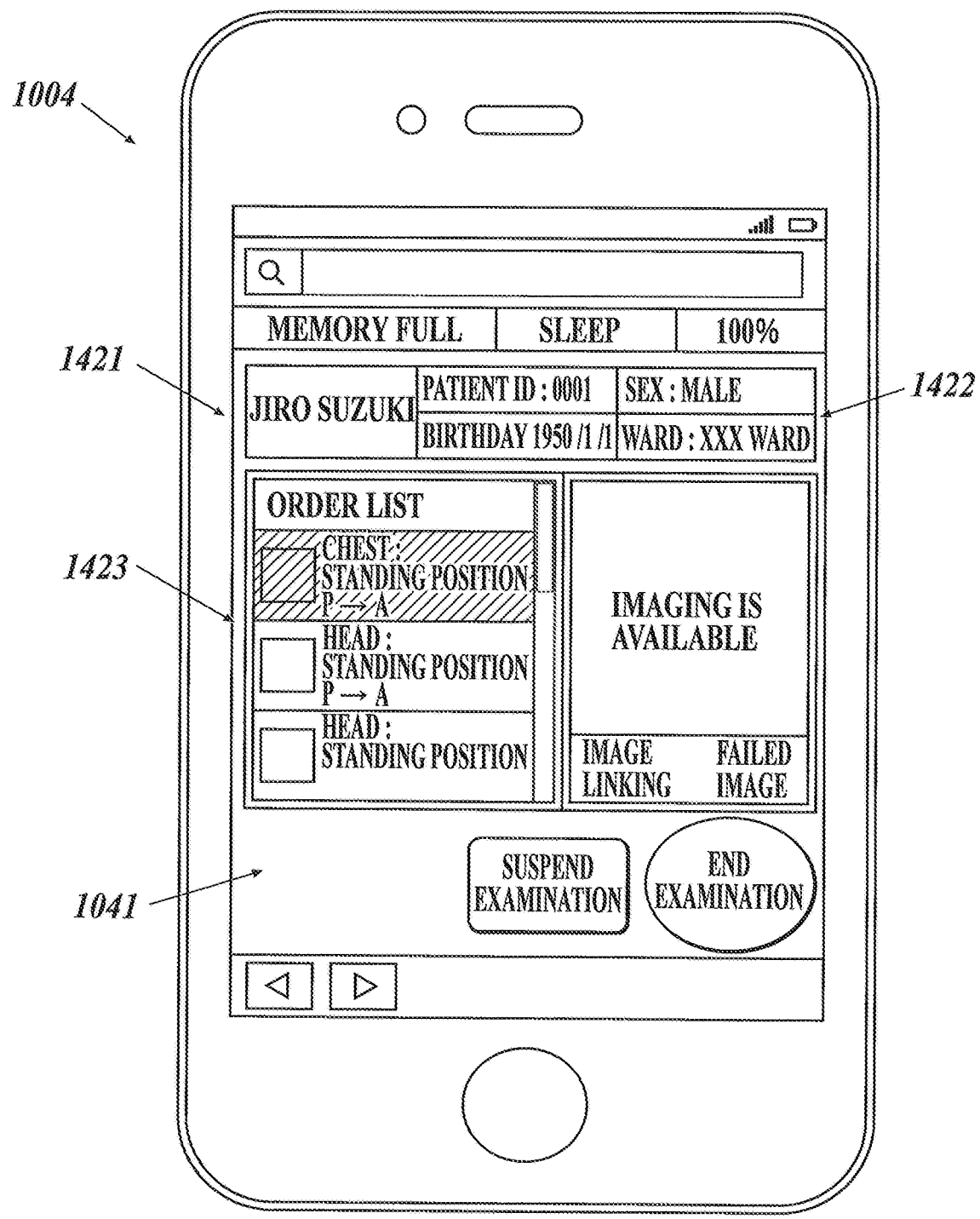
FIG. 15 shows an example of the display screen in an imaging order display processing.

FIG. 15 shows an example of the display screen in this embodiment showing that an imaging order information list screen 1421 is displayed on the display 1041 of the terminal apparatus 1004.

As shown in FIG. 15, the imaging order information list screen 1421 is provided with: a patient information display section 1422 where a patient name, a patient ID and so forth of a patient to be imaged are displayed; an imaging order display section 1423 where scheduled imaging orders of the patient, whose patient information is displayed in the patient information display section 1422, are displayed; and so forth.

Further, in this embodiment, as described below, a CGI execution request is set in such a way as to, when an imaging order is selected by a user operating the input operation unit 1042, such as a touchscreen, execute a CGI routine of an imaging execution request (imaging order).

This makes the input operation unit 1042 of the terminal apparatus 1004 function as a setting unit that sets arbitrary imaging order information (set imaging order information) among pieces of imaging order information.

In the CGI routine, the imaging execution request is designed to notify an imaging order ID selected by the imaging control program 1281 and request imaging. This design enables management of correlation of an imaging order selected (i.e. set imaging order information) by the Web browser function of the terminal apparatus 1004 with image data of a taken image obtained by imaging. The imaging order information set by the input operation unit 1042 and the image data of the taken image obtained by the radiation detector 1021 are correlated with one another and stored in an image-data plus imaging-order-ID storage 1036 by the imaging function unit 1251 as a storage control unit.

For example, if the shaded imaging order (chest, standing position, P→A) in the imaging order display section 1423 shown in FIG. 15 is selected by user's input operation, an imaging execution request for this imaging order is sent to the radiographic imaging apparatus 1002.

Figure 16:
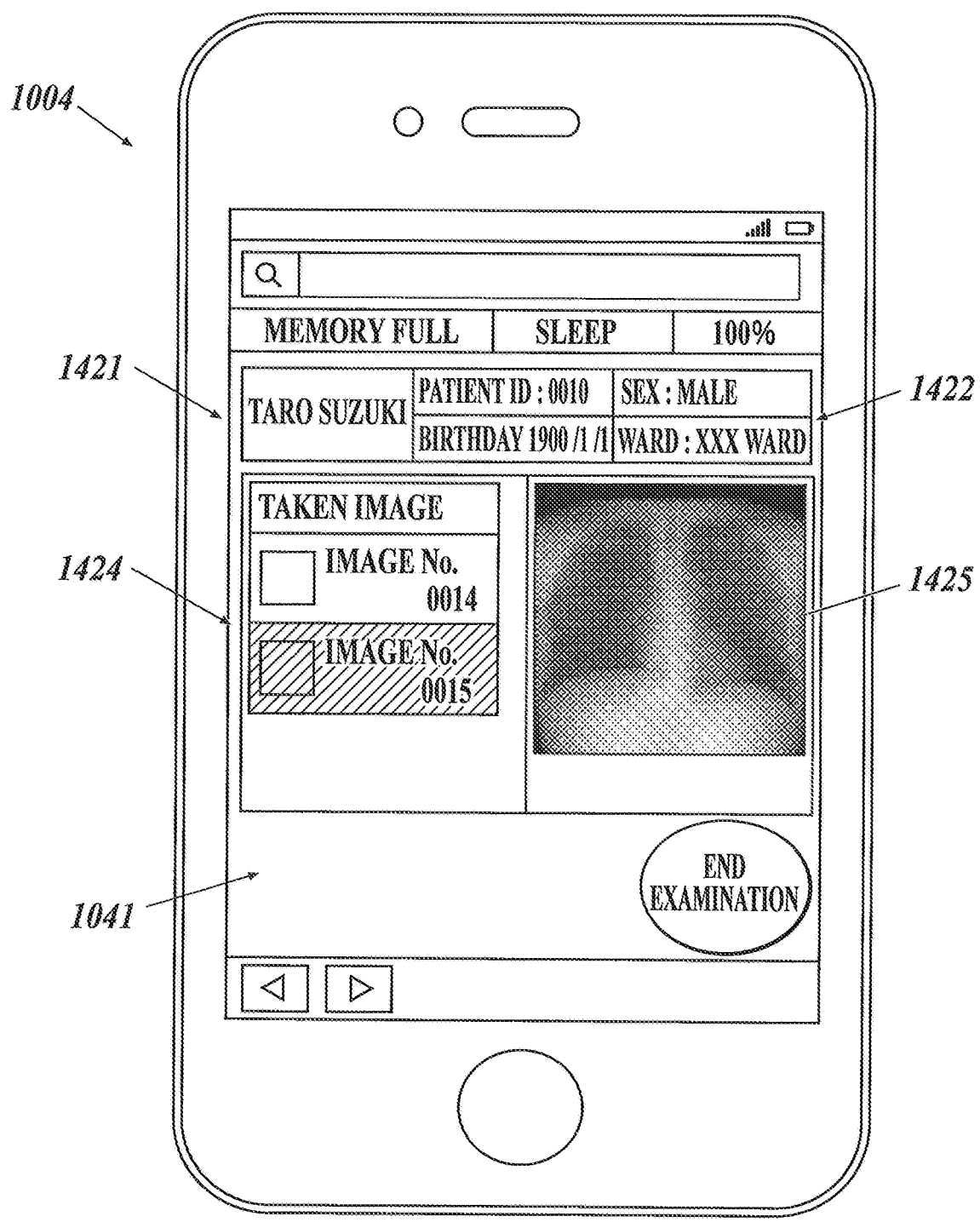
FIG. 16 shows an example of the display screen in the imaging order processing.

FIG. 16 shows a screen displayed on the display 1041 of the terminal apparatus 1004 after imaging performed in response to the imaging execution request.

On the display 1041, a taken image list display section 1424 is displayed, and also a taken image obtained on the basis of the imaging order is displayed in an imaging result display section 1425.

The radiographic imaging apparatus 1002 includes the image-data plus imaging-order-ID storage 1036 where image data of taken images are correlated and stored with their respective imaging order IDs. The radiographic imaging apparatus 1002 correlates each image data with an imaging order ID and stores the same in the image-data plus imaging-order-ID storage 1036.

The imaging function unit 1251 sends a set(s) of image data and an imaging order ID correlated with the image data, the set being stored in the image-data plus imaging-order-ID storage 1036, to the console 1006 at the timing when the radiographic imaging apparatus 1002 is connected to the console 1006. When receiving the image data and the imaging order ID from the radiographic imaging apparatus 1002, the control unit 1061 of the console 1006 stores these, which are in the correlated state, in an image-data plus imaging-order-ID storage 1063.

The other components are the same as those in the second embodiment. The same components are provided with the same reference numbers, and descriptions thereof are not repeated here.

[Operation of Radiograph Display System]

Next, operation of the radiograph display system 1010 of this embodiment is described with reference to FIG. 17 and so forth.

Figure 17:
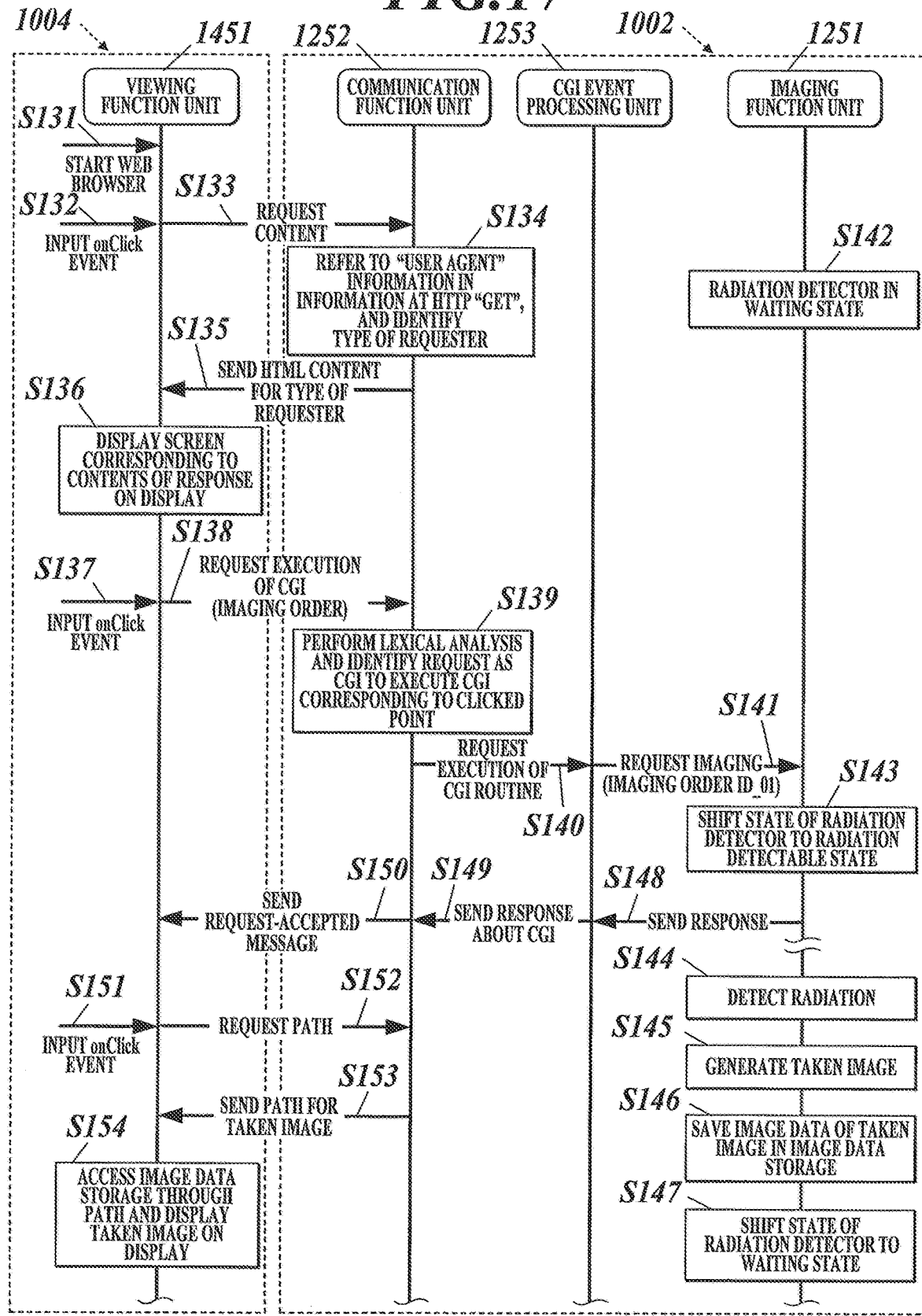
FIG. 17 is a sequence diagram showing a radiograph display process according to the third embodiment.

In this embodiment, when a radiograph display process to view taken images or the like on the portable terminal 1004 is performed, as shown in FIG. 17, as with the second embodiment, a Web browser of the terminal apparatus 1004 is started (Step S131), and a user inputs an onClick event through the input operation unit 1042, such as a touchscreen (Step S132). If the input event is a request for the viewing screen (main screen), the viewing function unit 1451 sends a content GET request ("HTTP "GET"", i.e. a request for the viewing screen (main screen)) to the communication function unit 1252 of the radiographic imaging apparatus 1002 (Step S133).

Steps S131 to S136 are almost the same as Steps S111 to S116 in FIG. 13 described in the second embodiment, and hence descriptions thereof are omitted.

As described above, in this embodiment, the HTML file (HTML content) sent to the viewing function unit 1451 in response to the content GET request contains the CGI execution request and JavaScript® for displaying the imaging order information on the display 1041 of the terminal apparatus 1004. This allows a user to view the imaging order information on the display 1041 of the terminal apparatus 1004, and also to select one of the imaging orders and request imaging (i.e. send an imaging execution request).

For example, if the imaging order information list screen 1421 shown in FIG. 16 is displayed on the display 1041 of the terminal apparatus 1004 and a user selects an imaging order (input operation) from the list, an event corresponding to the input operation is input (Step S137).

The viewing function unit 1451 analyzes contents of the event, which has been input on the basis of the form or the like of the operation to the input operation unit 1042, and if the event is a CGI execution request for an imaging order ID: 01, sends the CGI execution request ("HTTP "GET/ order.CGI?id=1"") to the communication function unit 1252 of the radiographic imaging apparatus 1002 (Step S138).

When receiving the CGI execution request from the viewing function unit 1451, the communication function unit 1252 performs lexical analysis on the request and identifies the request as a CGI, and determines to execute the CGI that corresponds to a click operation (touch operation) point where the input operation is performed (Step S139), and then requests the CGI event processing unit 1253 to execute a CGI routine (Step S140).

The instructed CGI event processing unit 1253 requests the imaging function unit 1251 to perform imaging for the imaging order ID: 01 (an imaging execution request for the imaging order ID: 01) (Step S141).

Then, the imaging function unit 1251 shifts the state of the radiation detector 1021 from the waiting state (Step S142) to the radiation detectable state (Step S143).

Steps S144 to S147 performed thereafter are almost the same as Steps S104 to S107 in FIG. 13 described in the second embodiment, and hence descriptions thereof are omitted.

When the radiation detector 1021 turns to the radiation detectable state, the imaging function unit 1251 sends a response to the CGI event processing unit 1253 to notify that the imaging execution request has been accepted (Step S148), and the CGI event processing unit 1253 sends a response to the communication function unit 1252 about the CGI event result (Step S149).

The communication function unit 1252 that has received the response sends a message that contents of the request have been accepted (HTTP "200 OK") to the viewing function unit 1451 of the terminal apparatus 1004 (Step S150).

If the user desires to display the taken image, which has been obtained by imaging performed in response to the imaging execution request (imaging order ID: 01), on the display 1041 of the terminal apparatus 1004, he/she selects, by an input operation, an item (e.g. the shaded imaging order in FIG. 15) corresponding to the imaging order ID: 01 in the imaging order display section 1423 shown in FIG. 15, thereby inputting an event by the input operation (Step S151).

When the event is input, the viewing function unit 1451 analyzes contents of the event, which has been input on the basis of the form or the like of the operation to the input operation unit 1042, and if the event is a request for the taken image obtained by imaging performed in response to the imaging order ID: 01, sends a Path GET request for the taken image to the communication function unit 1252 (Step S152).

When receiving the Path GET request from the viewing function unit 1451, the communication function unit 1252 sends a Path for the taken image to the viewing function unit 1451 of the terminal apparatus 1004 (Step S153).

When receiving the Path from the communication function unit 1252, the viewing function unit 1451 access the image-data plus imaging-order-ID storage 1036 of the radiographic imaging apparatus 1002 through the Path, and displays the taken image (e.g. in the imaging result display section 1425 shown in FIG. 16) on the display screen of the display 1041 (Step S154).

The other points are the same as those in the second embodiment, and hence descriptions thereof are not repeated here.

[Effects of Radiograph Display System]

As described above, this embodiment can obtain the following effects in addition to the same effects as those of the second embodiment.

That is, in this embodiment, the radiographic imaging apparatus 1002 includes the imaging order information storage 1037 where imaging order information on radiographic imaging is stored in the form to be providable for the terminal apparatus 1004.

This can provide the terminal apparatus 1004 with imaging order information without converting its data format or the like into another.

Further, in this embodiment, the communication function unit 1252 as the providing unit provides the terminal apparatus 1004 with the imaging order information stored in the imaging order information storage 1037 in response to a request(s) from the viewing function unit 1451, and the viewing function unit 1451 displays the imaging order information provided by the communication function unit 1252 on the display 1041.

This allows a user to readily confirm the imaging order information on the display 1041 of the terminal apparatus 1004 without going to the console 1006.

Further, in this embodiment, the present invention includes: the input operation unit 1042 as the setting unit that sets arbitrary imaging order information among pieces of imaging order information; and the imaging function unit 1251 as the storage control unit that correlates and stores data of a taken image obtained by the radiation detector 1021 with the imaging order information set by the input operation unit 1042.

Thus, when the input operation unit 1042 sets imaging order information, image data of a taken image obtained by imaging performed in response to the imaging order information (set imaging order information) is uniquely correlated with the imaging order information. This can eliminate risk of getting wrong imaging order information or image data of a taken image.

Further, in this embodiment, the terminal apparatus 1004 includes the input operation unit 1042 as the setting unit, and the viewing function unit 1451 sends the imaging order information set by the input operation unit 1042 to the communication function unit 1252 as the providing unit.

This can readily set an imaging order with the terminal apparatus 1004 at hand without the console 1006.

Further, in this embodiment, the radiation detector 1021 of the radiographic imaging apparatus 1002 turns to the imaging available state (i.e. the radiation detectable state) in response to the set imaging order information sent from the viewing function unit 1451 of the terminal apparatus 1004, and the imaging function unit 1251 as the storage control unit correlates and stores the set imaging order information with data of a taken image obtained by imaging performed in the imaging available state.

This allows a user to use, instead of the console 1006, the terminal apparatus 1004 at hand as a remote controller that easily controls imaging operation. Consequently, imaging at a place away from the console 1006 can be readily performed.

[Modifications of Radiographic Imaging Apparatus]

Although some embodiments of the present invention are described above, the present invention is not limited thereto, and, as a matter of course, can be modified in a variety of aspects without departing from the scope of the present invention.

For example, in the second and third embodiments, when receiving an HTML content GET request from the viewing function unit 1451 of the terminal apparatus 1004, the communication function unit 1252 having the Web server function identifies the type (screen size, resolution, etc.) of the requester from the information at the "HTTP GET", and sends content suitable for the type. However, the method for appropriate display for the screen size, the resolution and/or the like of the display 1041 of the terminal apparatus 1004 is not limited thereto.

For example, a description to automatically change the screen layout according to a viewing environment may be in the HTML content (or style sheet) itself (responsive web design).

In this case too, regardless of the type of the terminal apparatus 1004, a screen(s) can be displayed on the display 1041 by user-friendly screen layout, and the terminal apparatus 1004 in hand can be readily utilized as a monitor, which is convenience.

Further, in the third embodiment, the input operation unit 1042 of the terminal apparatus 1004 functions as the setting unit that sets imaging order information. Alternatively, the radiographic imaging apparatus 1002 may have an input operation unit as the setting unit.

In this case too, image data of a taken image obtained by imaging performed in response to the imaging order information is uniquely correlated with the imaging order information (set imaging order information). This can eliminate risk of getting wrong imaging order information or image data of a taken image.

Further, embedding a program language, such as JavaScript®, executable by the Web browser function of the terminal apparatus 1004 in the HTML content enables image processing, such as gradation manipulation (i.e. gradation processing), on a taken image(s) on the terminal apparatus 1004. Thus, the terminal apparatus 1004 can perform, by itself, the same process(es) (e.g. image processing) as the console 1006 does.

Further, on the display screen displayed as the HTML content, hyperlink destinations to various stores (e.g. APP Store, Google Play, etc.) may be written.

These various stores prepare dedicated application programs that enable advanced processes. Showing these various stores as the hyperlink destinations can be announcement for a user(s) who desires to do the advanced processes with the terminal apparatus 1004.

Further, by making full use of functions prepared in HTML5 or the like, a system in cooperation with a camera function and/or a code reader function of various codes which the terminal apparatus 1004 has may be constructed.

That is, for example, (i) taking, with the camera function, a picture(s) of a patient to be radiographically imaged, and/or (ii) attaching a wristband or the like having a barcode, a QR Code® or the like as identification information to an arm of the patient and reading the identification information with the camera or the like of the terminal apparatus 1004 can provide a function of storage of more detailed evidence and a function of more precise correlation (linking) of the patient with a taken image(s).

Although several embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Applications No. 2017-92168 filed on May 8, 2017 and No. 2017-145009 filed on Jul. 27, 2017 is incorporated herein by reference in its entirety.

What is claimed is:

1. A radiographic imaging apparatus comprising:
   a radiation detector including a substrate where radiation detection elements are arranged two-dimensionally, the radiation detection elements generating amounts of electric charges corresponding to doses of radiation by being irradiated with the doses of the radiation;
   a reader that reads the amounts of the electric charges generated by the radiation detection elements as signal values, and generates image data based on the signal values; and
   a hardware processor that:
      communicates with a portable terminal having a web browser;
      generates web content displayable on the web browser in response to a request from the portable terminal, said web content including a process program executable on the web browser, wherein the process program includes a process of performing image correction on the image data; and
      sends at least one of the web content and the image data to the portable terminal in response to the request from the portable terminal.

2. The radiographic imaging apparatus according to claim 1, wherein the hardware processor:
   receives external information from an external system;
   stores the external information and the image data in a storage; and sends at least one of the web content, the image data and the external information to the portable terminal in response to the request from the portable terminal.

3. The radiographic imaging apparatus according to claim 2, wherein the hardware processor sends the image data to the external system automatically or in response to the request from the portable terminal.

4. The radiographic imaging apparatus according to claim 2, wherein the hardware processor generates the web content containing the external information received from the external system.

5. A radiographic imaging system comprising:
the radiographic imaging apparatus according to claim 1; and
the portable terminal including a display and communicably connected with the radiographic imaging apparatus.

6. An information processing method using a radiographic imaging apparatus including a hardware processor that communicates with a portable terminal having a web browser, receives external information from an external system, and generates web content displayable on the web browser, comprising:

causing the radiographic imaging apparatus to receive the external information from the external system;

causing the radiographic imaging apparatus to generate the web content containing the received external information, said web content including a process program executable on the web browser, wherein the process program includes a process of performing image correction on the image data; and causing the radiographic imaging apparatus to send to the portable terminal the generated web content containing the external information and including the process program.

* * * * *